United States Patent [19]
Fesik et al.

[11] Patent Number: 5,891,643
[45] Date of Patent: Apr. 6, 1999

[54] USE OF NUCLEAR MAGNETIC RESONANCE TO DESIGN LIGANDS TO TARGET BIOMOLECULES

[75] Inventors: Stephen W. Fesik, Gurnee; Philip J. Hajduk, Palatine; Edward T. Olejniczak, Grayslake, all of Ill.

[73] Assignee: Abbott Laboratories, Abbott Park, Ill.

[21] Appl. No.: 558,633

[22] Filed: Nov. 14, 1995

[51] Int. Cl.$^6$ ............................ G01N 33/53; G01N 24/12
[52] U.S. Cl. ............................ 435/7.1; 436/501; 436/173
[58] Field of Search .............................. 435/7.1; 436/501, 436/173

[56] References Cited

U.S. PATENT DOCUMENTS

| | | | |
|---|---|---|---|
| 5,270,163 | 12/1993 | Gold et al. | 435/6 |
| 5,306,619 | 4/1994 | Edwards et al. | 435/6 |

FOREIGN PATENT DOCUMENTS

| | | |
|---|---|---|
| 9110140 | 7/1991 | WIPO . |
| 9300446 | 1/1994 | WIPO . |
| 9414980 | 7/1994 | WIPO . |
| 9418339 | 8/1994 | WIPO . |

OTHER PUBLICATIONS

Brown, S. C. et al., 15N NMR study of [15N]actinomycin D complexed with d(pGpC) and DNA J. Am. Chem. Soc. vol. 104 pp. 5504–5506.

Cheng J–W. et al. "15N NMR relaxation studies of the FK506 binding protein: Backbone dynamics of the uncomplexed receptor"Biochemistry vol. 32, pp. 9000–9010.

Gorenstein D. P. et al. "31P and two–dimensional 31P/1H correlated NMR spectra of duplex d(Ap[170]Gp[180]Cp[160]T) and assignment of 31P signals in d(ApGpCpT)2–actinomycin D complex" Biochemistry. vol. 23, pp. 6717–6723.

Lin C. H. et al. "Determination of the major tautomeric form of the covalently modified adenine in the (+)–CC–1065–DNA adduct by 1H and 15N NMR studies" Biochemistry vol. 29, pp. 9503–9507.

Nikonowicz, E. P. et al. "An efficient procedure for assignment of the proton, carbon and nitrogen resonances in 13C/15N labeled nucleic acids" J. Mol. Biol. vol. 232 pp. 1141–1156.

NMR Method Offers Shortcut To Drug Design; Science 274;1531 (1996).

Bennion, et al; Design and Synthesis of Some Substrate Analogue Inhibitors of Phospholipase A2 and Investigations by NMR and Molecular Modeling into the Binding Interactions in the Enxyme–Inhibitor Complex; J. Med. Chem 1992, 35, 2939–2951.

Fesik, eta l., NMR Methods for Determining the Structures of Enzyme/Inhibitor Complexes as an Aid in Drug Design; Biochem Pharm vol. 40, No. 1 pp. 161–167 1990.

Fesik, et al., NMR Studies of Molecular Complexes as a Tool in Drug Design; Journ of Med Chem vol. 34. No. 10 Oct. 1991 p. 2937.

Roberts et al.; Crystallization and Preliminary XRay Analysis of Elctron Transfer Flavoproteins from Human and Paracoccus Denitrificans; Protein Science(1995) 4:1654–1657.

Mujeeb, et al., A Potential Gene Target in HIV–1: Rationale, Selection of a Conserved Sequence. And Determination of NMR Distance and Torsion Angle Constraints. Biochemistry 1992, 31, 9325–9338.

Fesik, NMR Structure Based Drug Design, Journ of Bio NMR 3 (1993)261–269.

Sanner et al., Geom: A New Tool for Molecular Modelling Based on Distance Geometry Calculation with NMR Data, Journ of Computer–aided Molecular Design, 3 (1989) 195–210.

Journ of China Pharmaceutical Univeristy 1992: 23(5):316.

Craik et al., Determining the Conformation of a Ligand Bound to an Enzyme; Journ of Chem Ed. vol. 68 No. 3 Mar. 1991.

Zuiderweg, et al., Modern NMR Spectroscopy of Proteins and Peptides in Solution and Its Relevance to Drug Design; Perspecitives in Drug Disc and Design, 1 (1993) 391–417.

Trotta, et al., 1H NMR Study of [D(GCGATCGC);2 and Its Interaction with Minor Groove Binding 4', 6–Diamindino–2–Phenylindole, Journ of Biological Chemistry vol. 268 No. 6 Feb 25, pp 3944–3951.

Birdsall, NMR Spectroscopy and Drug Design: Lessons from Dihydrofolate Reductase Inhibitors.

Terry, et al., In Vivo Patent Infringement–Metabolic Pathways to Legal Trouble; Pharm News vol. 3., No. 4, 1996.

Erickson, CH 29 Macromolecular X–Ray Crystallography and NRM as Tool for Structure Based Drug Design; Annual Reports in Medicianl Chemistry 27 p. 271.

Reily, et al., Design, Synthesis and Solution Structure of a Renin Inhibitor . . . , FEBS vol. 302, No. 1, 97–103.

Mountzouris, et al., Comparison of a DSB–120 DNA Interstrand Cross–Linked Adduct with the Corresponding Bix–Tomaymycin Adduct: An Example of a Successful Template Directed Approach to Drug Design Based Upon the Monoalkylating Copound Tomaymycin, J. Med. Chem. 1994, 37, 3132–3140.

(List continued on next page.)

*Primary Examiner*—Lora M. Green
*Attorney, Agent, or Firm*—Jerry F. Janssen, Ph.D.; Frank Z. Yang; Lawrence S. Pope

[57] ABSTRACT

The present invention provides a process of designing compounds which bind to a specific target molecule. The process includes the steps of a) identifying a first ligand to the target molecule using two-dimensional $^{15}N/^{1}H$ NMR correlation spectroscopy; b) identifying a second ligand to the target molecule using two-dimensional $^{15}N/^{1}H$ NMR correlation spectroscopy; c) forming a ternary complex by binding the first and second ligands to the target molecule; d) determining the three dimensional structure of the ternary complex and thus the spatial orientation of the first and second ligands on the target molecule; and e) linking the first and second ligands to form the drug, wherein the spatial orientation of step (d) is maintained.

8 Claims, 10 Drawing Sheets

OTHER PUBLICATIONS

Angerman, et al., A Proton Magnetic Resonance Study of the Aggregation of Actinomycin D in D20+, Biochemistry vol. 11, No. 13, 1972.

Cheng, et al., 13N NMR Relaxation Studies of the FK506 Binding Protein: Dynamic Effects of Ligand Binding and Implications for Calcineurin Recognition, Biochem vol. 33, No. 14, 1994.

Folmer, et al, Solution Structure of the Single–Stranded DNA Binding Protein of the Filaentous Pseudomonas Phage PF3: Similarity to Other Proteins Binding to Single–Stranded Nucleic Acids: The EMBO Journ. vol. 14, No. 17. pp. 4132–4142, 1995.

Bycroft, et al; NMR Solution Structure of a DSRNA Binding Domain from Drosophila Staufen Protein Reveals Homology to the N–Terminal Domain of Ribosomal Protein S5; The EMBO Journ., vol. 14 No. 14 pp. 3563–3571, 1995.

Vis, et al.; Solution Structure of the Hu Protein from Bacillus Stearothermophilus; J. Mol. Biol. (1995) 254, 692–703.

Bushweller, et al.; The Nuclear Magnetic Resonance Solution Structure of the Mixed Disulfide Between *Escherichia Coli* Glutaredoxin (C14S) and Glutathione; J. Mol. Biol. (1994) 235,1585–1597.

van Nuland, et al.; The High–Resolution Structure of the Histidine–Containing Phosphocarrier Protein HPR from HPR from *Escherichia Coli* Determined by Restrained Molecular Dynamics from Nuclear Magnetic Resonance Nuclear Overhauser Effect Data; J. Mol. Biol. (1994) 237, 544–559.

Osapay, et al.; Solution Structure of Carbonmonoxy Myoglobin Determined from Nuclear Magnetic Resonance Distance and Chemical Shift Constraints; J. Mol. Biol. (1994) 244,183–197.

Schnuchel, et al.: Structure of Severin Domain 2 in Solution; J. Mol. Biol. (1995) 247,21–27.

Szyperski, et al, NMR Structure Determination of the *Escherichia Coli* DNAJ Molecular Chaperone: . . . , Proc. Natl. Acad. Sci. vol. 91, pp. 11242–11347 Nov. 1994.

Fushman, et al.; Solution Structure of Pleckstrin Homology Domain of Dynamin by Heteronuclear NMR Spectroscopy; Proc. Natl. Acad vol. 92, pp. 816–820 Jan. 1995.

Lodi, et al.; High–Resolution Solution Structure of the B Chemokine HMIP–1 B by Multidimensional NMR: Science vol. 263, 25 Mar. 1994.

Xu, et al.; Solution Structure of a Cellulose–Binding Domain from Cellulomonas Fimi by Nuclear Magnetoc Resonance Spectroscopy; Biochemistry 1995, 34, 6993–7009.

Kuboniwa, et al.; Solution Structure of Calcium Free Calmodulin; NAt Structural Biol vol. 2 No. 9 Sep. 1995.

Zhang, et al., Calcium Induced Conformational Transition Revealed by the Solution Structure of APO Calmodulin; Nat. Struc Bio. vol. 2 No. 9, Sep. 1995.

Newkirk, et al.; Solution NMR Structure of the Major Cold Shock Protein (CSPA) from *Escherichia Coli* : Identification of a Binding Epitope for DNA, Proc Natl Acad Sci vol. 91, pp. 5114–5118.

Morita, et al.; Structure of the OCT–3 POU–Homeodomain in Solution, as Determined by Triple Resonance Heteronuclear Multidimensional NMR Spectroscopy, Protein Science (1995) 4: 729–739.

Santoro, et al., Three–Dimensional Structure of Chemotactic CHE Y Protein in Aqueous Solution by Nuclear Magnetic Resonance Methods, J. Mol. Biol. (1995) 247, 717–725.

Skelton, et al., Determination of the Solution Structure of APO Calbindin D9K by NMR Spectroscopy; J. Mol. Biol. (1995) 249,441–462.

Tsao, et al., The Three–Dimensional Solution Structure of the NK–2 Homeodoamin from Drosophila; J. Mol. Biol. (1995) 251,297–307.

Pervushin, et al., Three–Dimensional Structure of (1–71) Bacterioopsin Solubilzed In Methanol . . . Eur. J. biochem 219, 517–583 (1994).

Sivaraja, et al., Solution Structure of POU–Specific Homeodomain: 3D–NMR Studied of Human B–Cell Transcription Factor OCT–2, Biochemistry 1994, 33, 9845–9855.

Kraulis, et al.: Solution Structure and Dynamics of RAS P21 GDP Determined by Heteronuclear Three and Four–Dimensional NMR Spectroscopy; Biochemistry 1994, 33. 3515–3531.

Narula, et al.; Three–Dimensional Solution Structure of Callinectes Sapidus Metallothionein–1 Determined by Homonuclear and Heternuclear Magnetic Resonance Spectroscopy; Biochemistry 1995, 34, 620–631.

Banci, et al., The Three–Dimensional Solution Structure of the Reduced High–Potential Iron–Sulfur Protein from Chromatium Vinosum Through NMR; Biochemistry 1995, 34, 206–219.

Cerf, et al., Homo and Heternuclear Two–Dimensional NMR Studies of the Globular Domain of Histon H1 . . . ; Biochemistry 1994, 33, 11079–11086.

Moy, et al., Assignments, Secondary Structure, Global Fold, and Dynamics of Chemotaxis Y Protein Using Three and Four Dimensional Heteronuclear (13C, 15N) NMR Spectroscopy; Biochemistry 1994, 33, 10731–10742.

Mayo, et al., NMR Solution Structure of the 32–KDA Platelet Factor 4 ELR–Motif N–Terminal Chimera: A Synnetric Tetramer; Biochemistry 1995, 34, 11399–11409.

Slupsky. et al.; NMR Solution Structure of Clacium Saturated Skeletal Muscle Troponin C: Biochemistry 1995, 34, 15953–15964.

Hardman, et al.; Structure of the A–Domain of HMG1 and Its Interaction with DNA as Studied by Heternuclear Three and Four Dimensional NMR Spectroscopy; Biochemistry 1995, 34, 16596–16607.

Rouviere Fourmy, et al., 1H and 15N Assignment of NMR Spectrum, Secondary Structure and Global Folding of the Immunophilin–Like Domain of the 59–KDA FK506–Binding Protein; Eur J. Biochem. 231, 761–772 (1995).

Greer, et al.; Application of the Three Dimensional Structures of Protein Target Molecules in Structure Based Drug Design#; Journ of Med Chem. vol. 37, No. 8 Apr. 15, 1994.

Ogata, et al.; Solution Structure of a Specific DNA Complex of the DNA–Binding Domain of MYB Oncoprotein by NMR; Nucleic Acids Symposium Series No. 31 217–218.

Lassen et al; Three Dimensional Structure of Bovine Heart Fatty Acid Binding Protein with Bound Palmitic Acid, Determined by Multidimensional NMR Spectroscopy; Eur. J. Biochem 230, 266–280 (1995).

Zhou, et al; Structure and Ligand Recognition of the Phosphotyrosine Binding Domain of SHC; Nature vol. 378 Dec. 7, 1995.

Clore et al., High Resolution Structure of the Oligomerization Domain of P53 by Multidimensional NMR; Science vol. 265 Jul. 1994.

Kaptein et al.,Structure and Dynamics of the Lac Repressor–Operator Complex as Determined by NMR; Toxicology Letter 82/83 (1995) 591–599.

Werner, et al.; The Solution Structure of the Human ETS1–DNA Complex Reveals a Novel Mode of Binding and True Side Chain Intercalation; Cell. vol. 83, 761–777 Dec. 1, 1995.

Atkinson, et al.; Echistatin: The Refined Structure of a Disintegrin in Solution by 1H NMR and Restrained Molecular Dynamics; Int J. Peptide Protein Res 43. 1994, 563–572.

Gincel, et al.; Three Dimensional Structure in Solution of a Wheat Lipid–Transfer Protein from Multidimensional 1H–NMR Data; Eur. J. Biochem 226, 413–422 (1994).

Banci et al; The Three Dimensional Structure in Solution of the Paramagnetic High Potential Iron Sulfur Protein I from Ectothiorhodospira Halophila Through Nuclear Magnetic Resonance; Eur. J. Biochem 225–725 (1994).

Yang et al., Solution Structure of Gap SH3 Domain by 1H NMR and Spatial Arrangement of Essential Ras Signaling–Involved Sequence; The EMBO Journ vol. 13, No. 6, pp. 1270–1279 (1994).

Fogh et al.; Solutiojn Structure of the Lexa Repressor DNA Binding Domain Determined by 1H NMR Spectroscopy; The EMBO Journ vol. 13 No. 17 pp. 3936–3944 1994.

Demene et al; Three Dimensional 1H NMR Structure of the Nucleocapsid Protein NCP10 of Moloney Murine Leukemia Virus; Journ of Biomole NMR, 4 (1994) 153–170.

Findlay et al; Solution Structure of the TR1C Fragment of Skeletal Muscle Troponin–C; The Journ of Biolo Chem. vol. 269, No. 9, Mar. 4 pp. 6773–6778 1994.

Cai et al; Solution Conformation of Cytochrome C–551 from Pseudomonas Stutzeri Zobell Determined by NMR; Biophysical Journal vol. 67 Sep. 1994 1207–1215.

Ottiger et al; The NMR Solution Structure of the Pheromone ER–2 from the Ciliated Protozoan Euplotes Raikovi; Protein Science (1994) 3: 1515–1526.

Qian et al; Nuclear Magnetic Resonance Solution Structure of the Fushi Tarazu Homeodomain from Drosophila and Comparison with the Antennapedia Homeodomain; J. Mol. Bio. 1994, 238, 333–345.

Barlow et al; Structure of the C3HC4 Domain by 1H–Nuclear Magnetic Resonance Spectroscopy; J. Mol. Biol. 1994 237, 201–211.

Campbell et al; Comparison of NMR Solution Structures of the Receptor Binding Doamins of Pseudomanas Aeruginosa Pili Straindpoa, KB7 and PAK Implications for Recepto Binding and Synthetic Vaccine Design; Biochemistry 1995, 34, 16255–16268.

Campos–Olivas et al, NMR Solution Stucture of the Antifungal Protein from Aspergillus Giganteus: Evidence for Cysteine Pairing Isomerism; Biochemistry 1995, 34, 3009–3021.

Wilson et al; A Determination of the Solution Conformation of the Nonmammalian Tachykinin Eledoisin by NRM and DC Spectroscopy; Biochemistry 1994, 33, 6802–6811.

Amodeo et al; Multiple Conformations and Proline Cis–Trans Isomerization in Salmon Calcitonin: a Combined Nuclear Magnetic Resonance, Distance Geometry, and Molecular Mechanics Study; Biochemistry 1994, 33, 10754–10762.

Hoffman et al., Crystal Structure of Prokaryotic Ribosomal Protein L9: A Bilobed RNA Binding Protein; The EMBO Journ vol. 13, No. 1 pp. 205–212, 1994.

Jia et al; Crystallization and Preliminary X–Ray Crystallographic Studies Type III Antifreeze Protein: Protein Science (1995), 4: 1236–1238.

Sohi et al., Crystallization and X–Ray Analysis of a Single FAB Binding Domain from Protein L of Peptostrptococcus Magnus; Proteins: Stucture, Function, and Genetic 23:610–612 (1995).

Ermler et al.; Crystallization and Preliminary X–Ray Diffraction Studies of a Bacterial Flavohemoglobin Protein; Proteins: Structure, Function and Genetics 21: 351–353 1995.

Choudhary et al.; Crystallization and Preliminary X–Ray Crystallographic Analysis of the 38–KDA Immunodominant Antigen of Mycobacterium Tuberculosis: Protein Science (1994) 3:2450–2451.

Thunnissen et al; Purification, Crystallisation And Preliminary X–Ray Analysis of Penicillin Binding Protein 4 From *Escherichia Coli*, a Protein Related to Class A B–Lactamases; J. Mol. Bio. 1995 247, 149–153.

Song et al.; Crystallization and Preliminary X–Ray Crystallographic Study of Ribosome–Inactivating Protein from Barley Seeds; Acta Cryst (1994) D50, 910–912.

Davies et al.; Crystallization and Preliminary XRay Diffraction Studies of Bacterial Ribosomal Protein L14; Acta Cryst (1994) D50, 790–792.

Inoue et al.; Refined Crystal Structure of Pseudoazurin from Methylobacterium Extorquens Am1 at 1.5 a Resolution; Acta Cryst 1994, D50, 317–328.

Jia et al.; Crystallization and Prelininary XRay Structure Solution of Rhizomucor Miehei Aspartic Proteinase; Acta Cryst (1995) D51, 243–244.

Verboven et al; Crystallization and XRay Investigation of Vitamin D–Binding Protein from Human Serum. Identification of the Crystal Content; J. Steroid Biochem Molec. Biol. vol. 54, No. 1/2 pp. 11–14 1995.

Thompson et al; Crystal Structure of Cellular Retinoic Acid Binding Protein I Shows Increased Access to the Binding Cavity Due to Formation of an Intermolecular B Sheet; J. Mol. Biol. (1995) 252, 433–446.

de Mel et al.; Crystallization and Preliminary XRay Diffraction Analysis of the Arsc Protein from the *Escherichia Coli* Arsenical Resistance Plasmid R773; J. Mol. Biol. (1994) 242, 701–702.

Greasley et al; Crystallization and Preliminary XRay Diffraction Studies on ADP Ribosylation Factor 1; J. Mol. Biol. (1994) 244, 651–653.

Picot et al.; The XRay Crystal Structure of the Membrane Protein Prostaglandin H2 Synthase–1; Nature vol. 367 Jan. 20, 1994.

Hopkins et al.; Crystallization and Preliminary XRay Analysis of C–Reactive Protein from Rat; J. Mol. Biol. (1994) 235,767–771.

Sierra et al: Crystallization and Preliminary XRay Investigation of a Recombinant Outer Membrane Protein from Neisseria Meningitidis; J. Mol. Biol. (1994) 235, 1154–1155.

Prakash et al.; Crystallization and Prelinimary XRay Diffraction Studies on a Trypsin/Chymotrypsin Double–Headed Inhibitor from Horse Gram; J. Mol. BIol. (1994) 235, 364–366.

Jedrzejas et al.; Crystallization and Preliminary XRay Diffraction Studies of the Cartilage Link Protein from Bovine Trachea; Proteins: Structure, Function, and Genetics 22:76–78 (1995).

Belyaev et al; Crystallization and Preliminary XRay Investigation of Recombinant Simian Immunodeficiency Virus Matrix Protein; J. Mol. Biol. (1994) 241, 744–746.

Englebert et al.; Crystallization and XRay Diffraction Study of the Streptomyces K15 Penicillin Binding DD Transpeptidase; J. Mol. Biol. (1994) 241, 295–297.

Chang et al; Crystallization and Preliminary XRay Analysis of a Trimeric Form of Human Mannose Binding Protein; J. Mol. Biol. (1994) 241, 125–127.

Lee–Huang et al; Crystallization and Preliminary XRay Analysis of Gap 31; J. Mol. Biol. (1994) 240, 92–94.

Zhang et al.; Crystallization and Preliminary XRay Analysis of the Low Molecular Weight Phosphtyrosyl Protein Phosphatase from Bovin Heart; J. Mol. Biol. (1994) 238,281–283.

Mosimann et al; Refined 1.6 A XRay Crystallographic Sturcture of P–30 Protein, an Amphibian Ribonuclease with Anti–Tumor Activity; J. Mol. Biol (1994) 236, 1141–1153.

Wagner et al; Crystallization and Preliminary XRay Diffraction Studies of a Corrinoid Protein from Sporomusa Ovata; J. Mol. Biol (1994) 236, 388–389.

Weisgraber et al; Crystallization and Preliminary XRay Analysis of Human Plasma Apolipoprotien C1; J. Mol. Biol. (1994) 236, 382–384.

St Charles et al; Crystallization and Preliminary XRay Analysis of APO–S100B and S100B with CA2+; J. Mol. Biol. (1994) 236.

Kondo et al; Crystallization and XRay Studies of the DNA Binding Domain of OMPR Protein a Positive Regulator Involved in Activation of Osmoregulatory Genes in *Escherichia Coli* ; J. Mol. Biol. (1994) 235, 780–782.

Borisova et al; Crystallization and Preliminary XRay Diffraction Studies of Teh Lepidopteran Specific Insecticidal Crystal Protein CRYLA (a); J. Mol.. Biol. (1994)243, 530–532.

Charon et al; Crystallization and Preliminary XRay Diffraction Study of the Nickel Binding Protein Nika of *Escherichia Coli* ; J. Mol. Biol. (1994) 243, 352–355.

Kumasaka et al; Crystallization and Preliminary XRay Study of H2–Proteinase from the Venom of Trimeresurau Flavoviridis; J. Biochem 117, 929–930 (1995).

de Mel et al; Preliminary XRay Diffraction Analysis of Crystals of the PII Protein from *Escherichia Coli* ; J. Mol. Biol. (1994) 243, 796–798.

Doukov et al; Preliminary XRay Crystallographic Study of Methyltetrahydrofolate:Corrinoid/Iron Sulfur Protien Methyltransferase from Clostridium Thermoaceticum; Acta Cryst (1995) D51, 1092–1093.

Vallee et al; Characterization, Crystallization and Preliminary XRay Crystallographic Analysis of the Complex Between Barley Amylase and the Bifunctional Amylase/Sybtilisin Inhibitor Form Barley Seeds; J. Mol. Biol. (1994) 236, 368–371.

Nardini et al; Reptile Heme Protein Structure: XRay Crystallographic Study of the Aquo–Met And Cyano–Met Derivatives of Teh Loggerhead Sea Turtle (Caretta Caretta) Myoglobin at 2.0 a Resolution; J. Mol. Biol. (1995) 247, 459–465.

Hyvonen et al; Structrure of the Binding Site for Inositol Phosphates in a PH Domain; The EMBO Journ vol. 14, No. 19 pp.4676–4685.

Kanellopoulos et al; Crystallization and Preliminary XRay Crystallographic Studies on the Adenovirus SSDNA Binding Protein in Complex with SSDNA; Journ of Struct Biol. 115, 113–116 (1995).

Li et al; Crystallization and Preliminary XRay Analysis of Borrelia Burgdorferi Outer Surface Protein A (OSPA) Complexed with a Murine Monoclonal Antibody FAB Fragment; Journ of Struc Biol 115, 335–337 (1995).

Pitts et al; The Three Dimensional XRay Crystal Structure of the Aspartic Proteinase Native to Trichoderma Reesei Complexed with a Renin Inhibitor CP–80794.

Li et al; Crystallization and Preliminary XRay Diffraction Studies of an A1/2/DNA Ternary Complex; Proteins: Structure, Function and Genetics 21: 161–164 (1995).

LaLonde et al; XRay Crystallographic Structures of Adipocyte Lipid–Binding Protein Complexed with Palmitate and Hexadencanesulfonic Acid Properties of Cavity Binding Sites; Biochemistry 1994, 33, 4885–4895.

Kitadokoro et al; Crystallization and Preliminary XRay Crystallographic Studies of Glutamic Acid Specific Proteinase from Bacillus Licheniformis Comples with Z–Leu–Glu–CH2CL; Acta Cryst (1995) D51, 835–836.

Derrick et al; The Third IgG Binding Domain from Streptococcal Pritein G an Analysis by XRay Crystallography of the Structure Alone and in a Complex with FAB; J. Mol. Biol. (1994) 243,906–918.

S.W. Fesik et al., "NMR Methods For Determining The Structures Of Enzyme/Inhibitor Complexes As An Aid In Drug Design", *Biochemical Pharmacology*, vol. 40, No. 1, 161–167 (1990).

R.P. Meadows et al., "Three–Dimensional Structure Of The FK506 Binding Protein/Ascomycin Complex In Solution By Heteronuclear Three–And Four–Dimensional NMR", *Biochemistry*, vol. 32, 754–765 (1993).

A. Bax et al., "Methodological Advances in Protein NMR", *Accounts of Chemical Research*, vol. 26, No. 4 (1993), pp. 131–138.

A. Bax et al., "An Efficient 3D NMR Technique for Correlating the Proton and $^{15}$N Backbone Amide Resonances With the α–Carbon of the Preceding Residue In Uniformly $^{15}$N/$^{13}$C Enriched Proteins", *Journal of Biomolecular NMR*, vol. 1, (1991), pp. 99–104.

A. Bax et al., "Optimized Recording of Heteronuclear Multidimensional NMR Spectra Using Pulsed Field Gradients", *Journal of Magnetic Resonance*, vol. 99, (1992), pp. 638–643.

G. Bodenhausen et al., "Natural Abundance Nitrogen–15 NMR by Enhanced Heteronuclear Spectroscopy", *Chemical Physics Letters*, vol. 69, No. 1, (1980), pp. 185–189.

S.D. Clark et al., "Coregulation of Collagenase and Collagenase Inhibitor Production by Phorbol Myristate Acetate in Human Skin Fibroblasts", *Archives of Biochemsitry and Biophysics*, vol. 241, No. 1, (1985), pp. 36–44.

D.A. Eagen et al., "Equilibrium Denaturation of Recombinant Human FK Binding Protein in Urea", *Biochemistry*, vol. 32, No. 8, (1993), pp. 1920–1927.

S.D. Emerson et al., "Solution Structure of the Ras–Binding Domain of c–Raf–1 and Identification of Its Ras Interaction Surface", *Biochemistry*, vol. 34, No. 21, (1995), pp. 6911–6918.

S.W. Fesik et al., "Heteronuclear Three–Dimensional NMR Spectroscopy. A Strategy for the Simplification of Homonuclear Two–Dimemsional NMR Spectra", *Journal of Magnetic Resonance*, vol. 78, No. 3, (1988), pp. 588–593.

G. Gemmecker et al., "An Improved Method for Selevtively Observing Protons Attached to $^{12}$C in the Presence of $^{1}$H–$^{13}$C Spin Pairs", *Journal of Magnetic Resonance*, vol. 96, (1992), pp. 199–204.

S. Grzesiek et al., "Correlating Backbone Amide and Side Chain Resonances in Larger Proteins by Multiple Relayed Triple Resonance NMR", *Journal of the American Chemicla Society*, vol. 114, (1992), pp. 6291–6293.

L.E. Kay et al., "Three–Dimensional Triple–Resonance NMR Spectroscopy of Isotopically Enriched Proteins", *Journal of Magnetic Resonance*, vol. 89, (1990), pp. 496–514.

L.E. Kay et al., "A Gradient–Enhanced HCCH–TOCSY Experiment for Recording Side–Chain $^1$H and $^{13}$C Correlations in H$_2$O Samples of Proteins", *Journal of Magnetic Resonance*, vol. 101, No. 6, (1993), pp. 333–337.

T.M. Logan et al., "Structural Characterization of the FK 506 Binding Protein Unfolded in Urea and Guanidine Hydrochloride", *Journal of Molecular Biology*, vol. 236, (1994), 637–648.

A.I. Marcy et al., "Human Fibroblast Stromelysin Catalytic Domain: Expression, Purification, and Characterization of a C–Terminally Truncated Form", *Biochemistry*, vol. 30, (1991), pp. 6476–6483.

D. Marion et al., "Three–Dimensional Heteronuclear NMR of $^{15}$N–Labeled Proteins", *Journal of the American Chemical Society*, vol. 111, (1989), pp. 1515–1517.

E.D. Matayoshi et al., "Novel Fluorogenic Substrates for Assaying Retroviral Proteases by Resonance Energy Transfer", *Science*, vol. 247, (1990), pp. 954–958.

D. Neri et al., "Stereospecific Nuclear Magnetic Resonance Assignments of the Methyl Groups of Valine and Leucine in the DNA–Binding Domain of the 434 Repressor by Biosynthetically Directed Fractional $^{13}$C Labelling", *Biochemistry*, vol. 28, (1989), pp. 7510–7516.

M. Nigles et al., "Determination of Three–Dimensional Structures of Proteins From Interproton Distance Data by Hybrid Distance Geometry–Dynamical Simulated Annealing Calculations", *FEBS LETTERS*, vol. 229, No. 2, (1988), pp. 317–324.

E.T. Olejniczak et al., "Extrapolation of Time–Domain Data With Linear Prediction Increases Resolution and Sensitivity", *Journal of Magnetic Resonance*, vol. 87, (1990), pp. 628–632.

Ye et al., "Purification and Characterization of the Human Stromelysin Catalytic Domain Expressed in *Escherichia Coli*", *Biochemistry*, vol. 31, (1992), pp. 11231–11235.

S.P. Rucker et al., "Broadband Homonuclear Cross Polarization in 2D N.M.R. Using DIPSI–2", *Molecular Physics*, vol. 68, No. 2, (1989), 509–517.

G.W. Vuister et al., "Quantitative J Correlation: A New Approach for Measuring Homonuclear Three–Bond J(H$^N$N$^\alpha$) Coupling Constants in $^{15}$N–Enriched Proteins", *Journal of American Chemical Society*, vol. 115, (1993), pp. 7772–7777.

H. Weingarten et al., "Spectrophotometric Assay for Vertebrate Collagenase", *Analytical Biochemistry*, vol. 147, No. 2, (1985), pp. 437–440.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
  ( A ) LENGTH: 174 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:1:

```
Phe Arg Thr Phe Pro Gly Ile Pro Lys Trp Arg Lys Thr His Leu Thr
1               5                   10                  15
Tyr Arg Ile Val Asn Tyr Thr Pro Asp Leu Pro Lys Asp Ala Val Asp
            20                  25                  30
Ser Ala Val Glu Lys Ala Leu Lys Val Trp Glu Glu Val Thr Pro Leu
        35                  40                  45
Thr Phe Ser Arg Leu Tyr Glu Gly Glu Ala Asp Ile Met Ile Ser Phe
    50                  55                  60
Ala Val Arg Glu His Gly Asp Phe Tyr Pro Phe Asp Gly Pro Gly Asn
65                  70                  75                  80
Val Leu Ala His Ala Tyr Ala Pro Gly Pro Gly Ile Asn Gly Asp Ala
                85                  90                  95
```

| His | Phe | Asp | Asp 100 | Asp | Glu | Gln | Trp | Thr 105 | Lys | Asp | Thr | Thr | Gly 110 | Thr | Asn |
|---|---|---|---|---|---|---|---|---|---|---|---|---|---|---|---|
| Leu | Phe | Leu 115 | Val | Ala | Ala | His | Glu 120 | Ile | Gly | His | Ser | Leu 125 | Gly | Leu | Phe |
| His | Ser | Ala 130 | Asn | Thr | Glu | Ala | Leu 135 | Met | Tyr | Pro | Leu | Tyr 140 | His | Ser | Leu |
| Thr 145 | Asp | Leu | Thr | Arg | Phe 150 | Arg | Leu | Ser | Gln | Asp 155 | Asp | Ile | Asn | Gly | Ile 160 |
| Gln | Ser | Leu | Tyr | Gly 165 | Pro | Pro | Pro | Asp | Ser 170 | Pro | Glu | Thr | Pro | | |

(2) INFORMATION FOR SEQ ID NO:2:

(i) SEQUENCE CHARACTERISTICS:
        (A) LENGTH: 83 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

| Met 1 | Ala | Thr | Thr | Pro 5 | Ile | Ile | His | Leu | Lys 10 | Gly | Asp | Ala | Asn | Ile 15 | Leu |
|---|---|---|---|---|---|---|---|---|---|---|---|---|---|---|---|
| Leu | Cys | Leu | Arg 20 | Tyr | Arg | Leu | Ser | Lys 25 | Tyr | Lys | Gln | Leu | Tyr 30 | Glu | Gln |
| Val | Ser | Ser 35 | Thr | Trp | His | Trp | Thr 40 | Cys | Thr | Asp | Gly | Lys 45 | His | Lys | Asn |
| Ala | Ile 50 | Val | Thr | Leu | Thr | Tyr 55 | Ile | Ser | Thr | Ser | Gln 60 | Arg | Asp | Asp | Phe |
| Leu 65 | Asn | Thr | Val | Lys | Ile 70 | Pro | Asn | Thr | Val | Ser 75 | Val | Ser | Thr | Gly | Tyr 80 |
| Met | Thr | Ile | | | | | | | | | | | | | |

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GAAATGAAGA GTCTTCAA                                            18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GCGTCCCAGG TTCTGGAG                                            18

(2) INFORMATION FOR SEQ ID NO:5:

(i) SEQUENCE CHARACTERISTICS:
        (A) LENGTH: 28 base pairs

-continued ( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:5:

ATACCATGGC CTATCCATTG GATGGAGC         28

( 2 ) INFORMATION FOR SEQ ID NO:6:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:6:

ATAGGATCCT TAGGTCTCAG GGGAGTCAGG         30

USE OF NUCLEAR MAGNETIC RESONANCE TO DESIGN LIGANDS TO TARGET BIOMOLECULES

TECHNICAL FIELD OF THE INVENTION

The present invention pertains to a method for the the use of two-dimensional $^{15}$N/$^{1}$H NMR correlation spectral analysis to design ligands that bind to a target biomolecule.

BACKGROUND OF THE INVENTION

One of the most powerful tools for discovering new drug leads is random screening of synthetic chemical and natural product databases to discover compounds that bind to a particular target molecule (i.e., the identification of ligands of that target). Using this method, ligands may be identified by their ability to form a physical association with a target molecule or by their ability to alter a function of a target molecule.

When physical binding is sought, a target molecule is typically exposed to one or more compounds suspected of being ligands and assays are performed to determine if complexes between the target molecule and one or more of those compounds are formed. Such assays, as is well known in the art, test for gross changes in the target molecule (e.g., changes in size, charge, mobility) that indicate complex formation.

Where functional changes are measured, assay conditions are established that allow for measurement of a biological or chemical event related to the target molecule (e.g., enzyme catalyzed reaction, receptor-mediated enzyme activation). To identify an alteration, the function of the target molecule is determined before and after exposure to the test compounds.

Existing physical and functional assays have been used successfully to identify new drug leads for use in designing therapeutic compounds. There are, however, limitations inherent to those assays that compromise their accuracy, reliability and efficiency.

A major shortcoming of existing assays relates to the problem of "false positives". In a typical functional assay, a "false positive" is a compound that triggers the assay but which compound is not effective in eliciting the desired physiological response. In a typical physical assay, a "false positive" is a compound that, for example, attaches itself to the target but in a non-specific manner (e.g., non-specific binding). False positives are particularly prevalent and problematic when screening higher concentrations of putative ligands because many compounds have non-specific affects at those concentrations.

In a similar fashion, existing assays are plagued by the problem of "false negatives", which result when a compound gives a negative response in the assay but which compound is actually a ligand for the target. False negatives typically occur in assays that use concentrations of test compounds that are either too high (resulting in toxicity) or too low relative to the binding or dissociation constant of the compound to the target.

Another major shortcoming of existing assays is the limited amount of information provided by the assay itself. While the assay may correctly identify compounds that attach to or elicit a response from the target molecule, those assays typically do not provide any information about either specific binding sites on the target molecule or structure activity relationships between the compound being tested and the target molecule. The inability to provide any such information is particularly problematic where the screening assay is being used to identify leads for further study.

It has recently been suggested that X-ray crystallography can be used to identify the binding sites of organic solvents on macromolecules. However, this method cannot determine the relative binding affinities at different sites on the target. It is only applicable to very stable target proteins that do not denature in the presence of high concentrations of organic solvents. Moreover, this approach is not a screening method for rapidly testing many compounds that are chemically diverse, but is limited to mapping the binding sites of only a few organic solvents due to the long time needed to determine the individual crystal structures.

Compounds are screened to identify leads that can be used in the design of new drugs that alter the function of the target biomolecule. Those new drugs can be structural analogs of identified leads or can be conjugates of one or more such lead compounds. Because of the problems inherent to existing screening methods, those methods are often of little help in designing new drugs.

There continues to be a need to provide new, rapid, efficient, accurate and reliable means of screening compounds to identify and design ligands that specifically bind to a particular target.

BRIEF SUMMARY OF THE INVENTION

In its principal aspect, the present invention provides a process for the design and identification of compounds which bind to a given target biomolecule. for biological activity to identify ligands that bind to a specific target molecule. That process comprises the steps of: a) identifying a first ligand to the target molecule using two-dimensional $^{15}$N/$^{1}$H NMR correlation spectroscopy; b) identifying a second ligand to the target molecule using two-dimensional $^{15}$N/$^{1}$H NMR correlation spectroscopy; c) forming a ternary complex by binding the first and second ligands to the target molecule; d) determining the three dimensional structure of the ternary complex and thus the spatial orientation of the first and second ligands on the target molecule; e) linking the first and second ligands to form the drug, wherein the spatial orientation of step (d) is maintained.

This aspect of the present invention uses the two-dimensional $^{15}$N/$^{1}$H NMR correlation spectroscopic screening process as set forth below to identify a first and subsequent ligands that bind to the target molecule. A complex of the target molecule and two or more ligands is formed and the three-dimensional structure of that complex is determined preferably using NMR spectroscopy or X-ray crystallography. That three-dimensional structure is used to determine the spatial orientation of the ligands relative to each other and to the target molecule.

Based on the spatial orientation, the ligands are linked together to form the drug. The selection of an appropriate linking group is made by maintaining the spatial orientation of the ligands to one another and to the target molecule based upon principles of bond angle and bond length information well known in the organic chemical art.

Thus, the molecular design aspect of the present invention comprises identifying a first ligand moiety to the target molecule using two-dimensional $^{15}$N/$^{1}$H NMR correlation spectroscopy; identifying subsequent ligand moieties to the target molecule using two-dimensional $^{15}$N/$^{1}$H NMR correlation spectroscopy; forming a complex of the first and subsequent ligand moieties to the target molecule; determining the three dimensional structure of the complex and, thus, the spatial orientation of the first and subsequent ligand moieties on the target molecule; and linking the first and subsequent ligand moieties to form the drug to maintain the spatial orientation of the ligand moieties.

The identification of subsequent ligand moieties can be performed in the absence or presence of the first ligand (e.g., the target molecule can be bound to the first ligand before being exposed to the test compounds for identification of the second ligand).

The present invention further contemplates a drug designed by the design process of this invention.

Chemical compounds can be screened for binding to a given target biomolecule by a process involving the steps of a) first generating a first two-dimensional $^{15}N/^1H$ NMR correlation spectrum of a $^{15}N$-labeled target molecule; b) exposing the labeled target molecule to one or a mixture of chemical compounds; c) next, generating a second two-dimensional $^{15}N/^1H$ NMR correlation spectrum of the labeled target molecule that has been exposed to one or a mixture of compounds in step (b); and d) comparing said first and second two-dimensional $^{15}N/^1H$ NMR correlation spectra to determine differences between said first and said second spectra, the differences identifying the presence of one or more compounds that are ligands which have bound to the target molecule.

Where the process screens more than one compound in step (b), that is, a mixture of compounds, and where a difference between the first spectrum generated from the target molecule alone and that generated from the target molecule in the presence of the mixture, additional steps are performed to identify which specific compound or compounds contained in the mixture is binding to the target molecule. Those additional steps comprise the steps of e) exposing the $^{15}N$-labeled target molecule individually to each compound of the mixture, f) generating a two-dimensional $^{15}N/^1H$ NMR correlation spectrum of the labeled target molecule that has been individually exposed to each compound; and g) comparing each spectrum generated in step f) to the first spectrum generated from the target molecule alone to determine differences in any of those compared spectra, the differences identifying the presence of a compound that is a ligand which has bound to the target molecule.

Because the chemical shift values of the particular $^{15}N/^1H$ signals in the two-dimensional correlation spectrum correspond to known specific locations of atomic groupings in the target molecule (e.g., the N-H atoms of the amide or peptide link of a particular amino acid residue in a polypeptide), the screening process allows not only for the for identification of which compound(s) bind to a particular target molecule, but also permit the determination of the particular binding site of the ligand on the target molecule.

The dissociation constant, $K_D$, for a given ligand and its target molecule can be determined by this process, if desired, by performing the steps of a) generating a first two-dimensional $^{15}N/^1H$ NMR correlation spectrum of a $^{15}N$-labeled target molecule; b) exposing the labeled target molecule to various concentrations of a ligand; c) generating a two-dimensional $^{15}N/^1H$ NMR correlation spectrum at each concentration of ligand in step (b); d) comparing each spectrum from step (c) to the first spectrum from step (a); and e) calculating the dissociation constant between the target molecule and the ligand from those differences according to the equation:

$$K_D = \frac{([P]_o - x)([L]_o - x)}{x}$$

An advantageous capability of the screening method is its ability to determine the dissociation constant of one ligand of the target molecule in the presence of a second molecule already bound to the ligand. This is generally not possible with prior art methods which employ "wet chemical" analytical methods of determining binding of a ligand to a target molecule substrate.

The process of determining the dissociation constant of a ligand can be performed in the presence of a second bound ligand. Accordingly, the $^{15}N$-labeled target molecule is bound to that second ligand before exposing that target to the test compounds.

The ability of the screening method to determine not only the existence of binding between one ligand and the target molecule, but also the particular site of binding in the presence of a second bound ligand, permits the capability to design a drug that comprises two or more linked moieties made up of the ligands.

In a preferred embodiment of the present invention, the target molecule used in the molecular design process is a polypeptide. The polypeptide target is preferably produced in recombinant form from a host cell transformed with an expression vector that contains a polynucleotide that encodes the polypeptide, by culturing the transformed host cell in a medium that contains an assimilable source of $^{15}N$ such that the recombinantly produced polypeptide is labeled with $^{15}N$.

BRIEF DESCRIPTION OF THE DRAWINGS

In the drawings which form a portion of the specification.

DETAILED DESCRIPTION OF THE INVENTION

Figure 1:
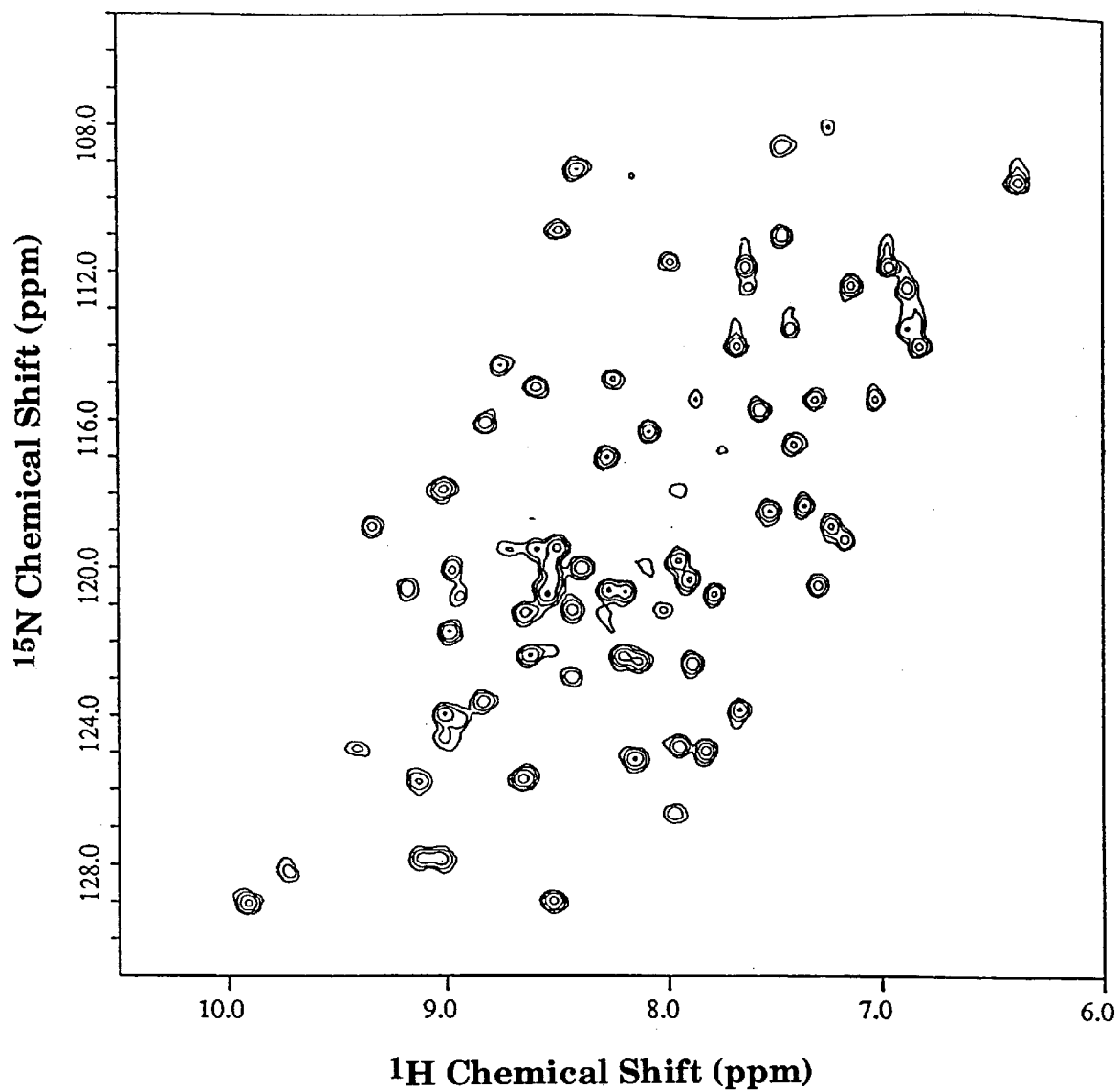
FIG. 1 shows a $^{15}N/^1H$ correlation spectrum of the DNA binding domain of uniformly $^{15}N$-labeled human papillomavirus E2. The spectrum (80 complex points, 4 scans/fid) was acquired on a 0.5 mM sample of E2 in 20 mM phosphate (pH 6.5), 10 mM dithiothreitol (DTT) and 10% deuterium oxide ($D_2O$).

The present invention provides a rapid and efficient method for designing ligands that bind to therapeutic target molecules.

Ligands are identified by testing the binding of molecules to a target molecule (e.g., protein, nucleic acid, etc.) by following, with nuclear magnetic resonance (NMR) spectroscopy, the changes in chemical shifts of the target molecule upon the addition of the ligand compounds in the database.

From an analysis of the chemical shift changes of the target molecule as a function of ligand concentration, the binding affinities of ligands for biomolecules are also determined.

The location of the binding site for each ligand is determined from an analysis of the chemical shifts of the biomolecule that change upon the addition of the ligand and from nuclear Overhauser effects (NOEs) between the ligand and biomolecule.

Information about the structure/activity relationships between ligands identified by such a process can then be used to design new drugs that serve as ligands to the target molecule. By way of example, where two or more ligands to a given target molecule are identified, a complex of those ligands and the target molecule is formed. The spatial orientation of the ligands to each other as well as to the target molecule is derived from the three-dimensional structure. That spatial orientation defines the distance between the binding sites of the two ligands and the orientation of each ligand to those sites.

Using that spatial orientation data, the two or more ligands are then linked together to form a new ligand. Linking is accomplished in a manner that maintains the spatial orientation of the ligands to one another and to the target molecule.

There are numerous advantages to the NMR-based discovery and design processes of the present invention. First, because a process of the present invention identifies ligands by directly measuring binding to the target molecule, the problem of false positives is significantly reduced. Because the present process identifies specific binding sites to the target molecule, the problem of false positives resulting from the non-specific binding of compounds to the target molecule at high concentrations is eliminated.

Second, the problem of false negatives is significantly reduced because the present process can identify compounds that specifically bind to the target molecule with a wide range of dissociation constants. The dissociation or binding constant for compounds can actually be determined with the present process.

Other advantages of the present invention result from the variety and detailed data provided about each ligand from the discovery and design processes.

Because the location of the bound ligand can be determined from an analysis of the chemical shifts of the target molecule that change upon the addition of the ligand and from nuclear Overhauser effects (NOEs) between the ligand and biomolecule, the binding of a second ligand can be measured in the presence of a first ligand that is already bound to the target. The ability to simultaneously identify binding sites of different ligands allows a skilled artisan to 1) define negative and positive cooperative binding between ligands and 2) design new drugs by linking two or more ligands into a single compound while maintaining a proper orientation of the ligands to one another and to their binding sites.

Further, if multiple binding sites exist, the relative affinity of individual binding moieties for the different binding sites can be measured from an analysis of the chemical shift changes of the target molecule as a function of the added concentration of the ligand. By simultaneously screening numerous structural analogs of a given compound, detailed structure/activity relationships about ligands is provided.

In part, the present invention provides a process of screening compounds to identify ligands that bind to a specific target molecule. That process comprises the steps of: a) generating a first two-dimensional $^{15}N/^1H$ NMR correlation spectrum of a $^{15}N$-labeled target molecule; b) exposing the labeled target molecule to one or more compounds; c) generating a second two-dimensional $^{15}N/^1H$ NMR correlation spectrum of the labeled target molecule that has been exposed to the compounds of step (b); and d) comparing the first and second spectra to determine whether differences in those two spectra exist, which differences indicate the presence of one or more ligands that have bound to the target molecule.

Where a process of the present invention screens more than one compound in step (b) and where a difference between spectra is observed, additional steps are performed to identify which specific compound is binding to the target molecules. Those additional steps comprise generating a two-dimensional $^{15}$N/$^1$H NMR correlation spectrum for each individual compound and comparing each spectrum to the first spectrum to determine whether differences in any of those compared spectra exist, which differences indicate the presence of a ligand that has bound to the target molecule.

Any $^{15}$N-labeled target molecule can be used in a process of the present invention. Because of the importance of proteins in medicinal chemistry, a preferred target molecule is a polypeptide. The target molecule can be labeled with $^{15}$N using any means well known in the art. In a preferred embodiment, the target molecule is prepared in recombinant form using transformed host cells. In an especially preferred embodiment, the target molecule is a polypeptide. Any polypeptide that gives a high resolultion NMR spectrum and can be partially or uniformly labeled with $^{15}$N can be used. The preparation of uniformly 15N-labeled exemplary polypeptide target molecules is set forth hereinafter in the Examples.

A preferred means of preparing adequate quantities of uniformly $^{15}$N-labeled polypeptides is to transform a host cell with an expression vector that contains a polynucleotide that encodes that polypeptide and culture the transformed cell in a culture medium that contains assimilable sources of $^{15}$N. Assimilable sources of $^{15}$N are well known in the art. A preferred such source is $^{15}$NH$_4$Cl.

Means for preparing expression vectors that contain polynucleotides encoding specific polypeptides are well known in the art. In a similar manner, means for transforming host cells with those vectors and means for culturing those transformed cells so that the polypeptide is expressed are also well known in the art.

The screening process begins with the generation or acquisition of a two-dimensional $^{15}$N/$^1$H correlation spectrum of the labeled target molecule. Means for generating two-dimensional $^{15}$N/$^1$H correlation spectra are well known in the art [See, e.g., D. A. Egan et al., Biochemistry, 32:8, pgs. 1920–1927 (1993); Bax. A., Grzesiek, S., Acc. Chem. Res., 26:4, pgs. 131–138 (1993)].

The NMR spectra that are typically recorded in the screening procedure of the present invention are two-dimensional $^{15}$N/$^1$H heteronuclear single quantum correlation (HSQC) spectra. Because the $^{15}$N/$^1$H signals corresponding to the backbone amides of the proteins are usually well-resolved, the chemical shift changes for the individual amides are readily monitored.

In generating such spectra, the large water signal is suppressed by spoiling gradients. To facilitate the acquisition of NMR data on a large number of compounds (e.g., a database of synthetic or naturally occurring small organic compounds), a sample changer is employed. Using the sample changer, a total of 60 samples can be run unattended. Thus, using the typical acquisition parameters (4 scans per free induction decay (fid), 100–120 HSQC spectra can be acquired in a 24 hour period.

To facilitate processing of the NMR data, computer programs are used to transfer and automatically process the multiple two-dimensional NMR data sets, including a routine to automatically phase the two-dimensional NMR data.

The analysis of the data can be facilitated by formatting the data so that the individual HSQC spectra are rapidly viewed and compared to the HSQC spectrum of the control sample containing only the vehicle for the added compound (DMSO), but no added compound. Detailed descriptions of means of generating such two-dimensional $^{15}$N/$^1$H correlation spectra are set forth hereinafter in the Examples.

A representative two-dimensional $^{15}$N/$^1$H NMR correlation spectrum of an $^{15}$N-labeled target molecule (polypeptide) is shown in FIG. 1 (the DNA-binding domain of the E2 protein).

Following acquisition of the first spectrum, the labeled target molecule is exposed to one or more test compounds. Where more than one test compound is to be tested simultaneously, it is preferred to use a database of compounds such as a plurality of small molecules. Such molecules are typically dissolved in perdeuterated dimethylsulfoxide. The compounds in the database can be purchased from vendors or created according to desired needs.

Individual compounds can be selected inter alia on the basis of size (molecular weight=100–300) and molecular diversity. Compounds in the collection can have different shapes (e.g., flat aromatic rings(s), puckered aliphatic rings (s), straight and branched chain aliphatics with single, double, or triple bonds) and diverse functional groups (e.g., carboxylic acids, esters, ethers, amines, aldehydes, ketones, and various heterocyclic rings) for maximizing the possibility of discovering compounds that interact with widely diverse binding sites.

The NMR screening process utilizes ligand concentrations ranging from about 0.1 to about 10.0 mM. At these concentrations, compounds which are acidic or basic can significantly change the pH of buffered protein solutions. Chemical shifts are sensitive to pH changes as well as direct binding interactions, and "false positive" chemical shift changes, which are not the result of ligand binding but of changes in pH, can therefore be observed. It is thus necessary to ensure that the pH of the buffered solution does not change upon addition of the ligand. One means of controlling pH is set forth below.

Compounds are stored at 263° K as 1.0 and 0.1M stock solutions in dimethylsulfoxide (DMSO). This is necessary because of the limited solubility of the ligands in aqueous solution. It is not possible to directly adjust the pH of the DMSO solution. In addition, HCl and NaOH form insoluble salts in DMSO, so alternative acids and bases must be used. The following approach has been found to result in stable pH.

The 1.0M stock solutions in DMSO are diluted 1:10 in 50 mM phosphate, pH 7.0. The pH of that diluted aliquot solution is measured. If the pH of the aliquot is unchanged (i.e., remains at 7.0), a working solution is made by diluting the DMSO stock solution 1:10 to make a 0.1M solution and that solution is stored.

If the pH of the diluted aliquot is less than 7.0, ethanolamine is added to the 1.0M stock DMSO solution, that stock solution is then diluted 1:10 with phosphate buffer to make another aliquot, and the pH of the aliquot rechecked.

If the pH of the diluted aliquot is greater than 7.0, acetic acid is added to the 1.0M stock DMSO solution, that stock solution is then diluted 1:10 with phosphate buffer to make another aliquot, and the pH of the aliquot rechecked.

Ethanolamine and acetic acid are soluble in DMSO, and the proper equivalents are added to ensure that upon transfer to aqueous buffer, the pH is unchanged. Adjusting the pH is an interactive process, repeated until the desired result is obtained.

Note that this procedure is performed on 1:10 dilutions of 1.0M stock solutions (100 mM ligand) to ensure that no pH changes are observed at the lower concentrations used in the experiments (0.1 to 10 mM) or in different/weaker buffer systems.

Following exposure of the $^{15}$N-labeled target molecule to one or more test compounds, a second two-dimensional $^{15}$N/$^1$H NMR correlation spectrum is generated. That second spectrum is generated in the same manner as set forth above. The first and second spectra are then compared to determine whether there are any differences between the two spectra. Differences in the two-dimensional $^{15}$N/$^1$H NMR correlation spectra that indicate the presence of a ligand correspond to $^{15}$N-labeled sites in the target molecule. Those differences are determined using standard procedures well known in the art.

By way of example, FIGS. 2, 3, 4, 5 and 6 show comparisons of correlation spectra before and after exposure of various target molecules to various test compounds. A detailed description of how these studies were performed can be found hereinafter in Examples 2 and 3.

Particular signals in a two-dimensional $^{15}$N/$^1$H correlation spectrum correspond to specific nitrogen and proton atoms in the target molecule (e.g., particular amides of the amino acid residues in the protein). By way of example, it can be seen from FIG. 2 that chemical shifts in a two-dimensional $^{15}$N/$^1$H correlation of the DNA-binding domain of E2 exposed to a test compound occurred at residue positions 15 (I15), 21 (Y21), 22 (R22) and 23 (L23).

Figure 2:
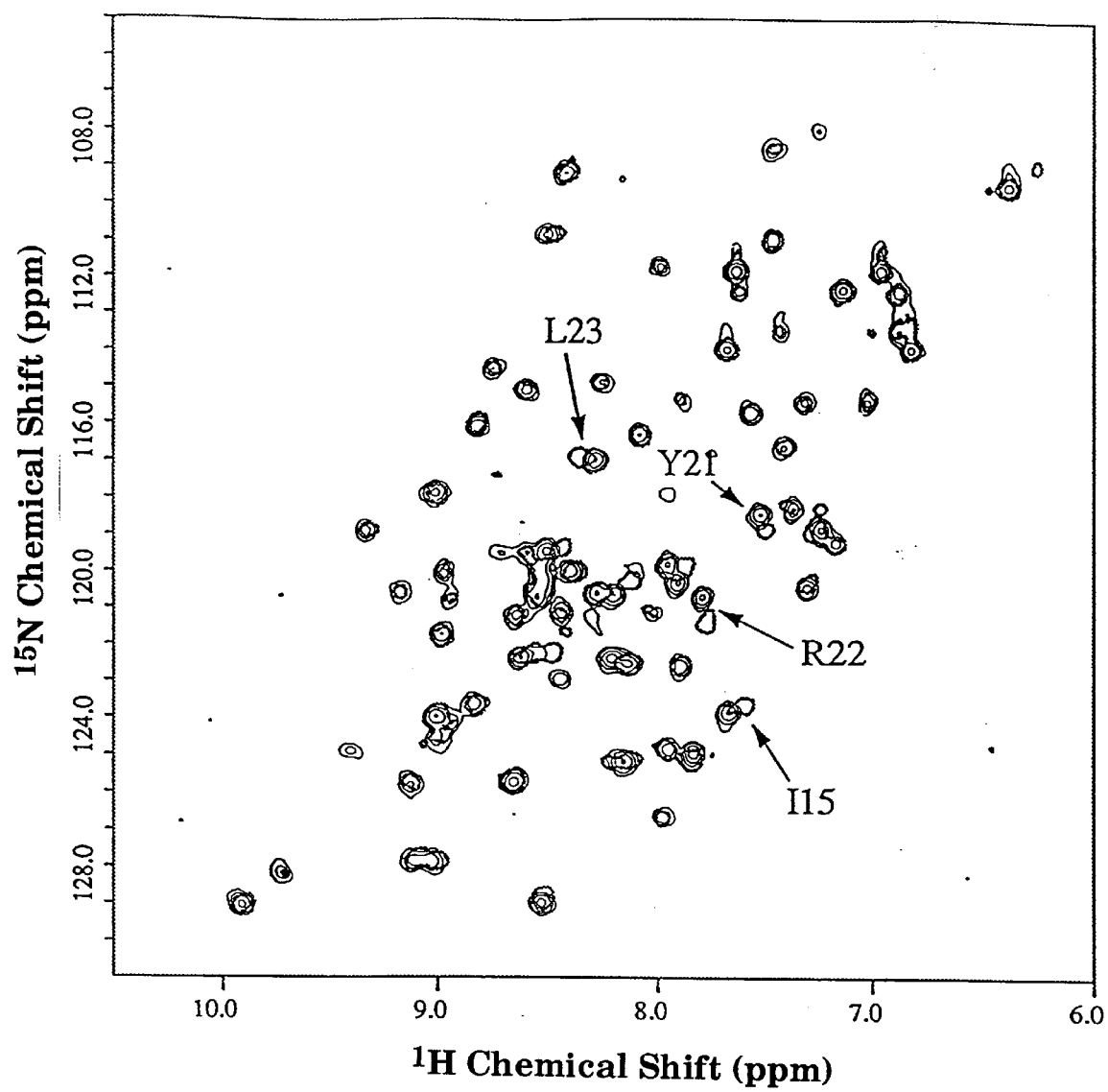
FIG. 2 shows $^{15}N/^1H$ correlation spectra of the DNA binding domain of uniformly $^{15}N$-labeled human papillomavirus E2 before (thin multiple contours) and after (thick single contours) addition of a final test compound. The final concentration of compound was 1.0 mM. All other conditions are as stated in FIG. 1. Selected residues that show significant changes upon binding are indicated.

It can be seen from FIG. 2 that the binding of the ligand involved the isoleucine (Ile) residue at position 15, the tyrosine (Tyr) residue at position 21, the arginine (Arg) residue at position 22 and the leucine (Leu) residue at position 23. Thus, a process of the present invention can also be used to identify the specific binding site between a ligand and target molecule.

The region of the protein that is responsible for binding to the individual compounds is identified from the particular amide signals that change upon the addition of the compounds. These signals are assigned to the individual amide groups of the protein by standard procedures using a variety of well-established heteronuclear multi-dimensional NMR experiments.

To discover molecules that bind more tightly to the protein, molecules are selected for testing based on the structure/activity relationships from the initial screen and/or structural information on the initial leads when bound to the protein. By way of example, the initial screening may result in the identification of ligands, all of which contain an aromatic ring. The second round of screening would then use other aromatic molecules as the test compounds.

As set forth hereinafter in Example 2, an initial screening assay for binding to the catalytic domain of stromelysin identified two biaryl compounds as ligands. The second round of screening thus used a series of biaryl derivatives as the test compounds.

The second set of test compounds are initially screened at a concentration of 1 mM, and binding constants are measured for those that show affinity. Best leads that bind to the protein are then compared to the results obtained in a functional assay. Those compounds that are suitable leads are chemically modified to produce analogs with the goal of discovering a new pharmaceutical agent.

The present method also provides a process for determining the dissociation constant between a target molecule and a ligand that binds to that target molecule. That process comprises the steps of: a) generating a first two-dimensional $^{15}$N/$^1$H NMR correlation spectrum of a $^{15}$N-labeled target molecule; b) titrating the labeled target molecule with various concentrations of a ligand; c) generating a two-dimensional $^{15}$N/$^1$H NMR correlation spectrum at each concentration of ligand from step (b); d) comparing each spectrum from step (c) both to the first spectrum from step (a) and to all other spectra from step (c) to quantify differences in those spectra as a function of changes in ligand concentration; and e) calculating the dissociation constant ($K_D$) between the target molecule and the ligand from those differences.

Because of their importance in medicinal chemistry, a preferred target molecule for use in such a process is a polypeptide. In one preferred embodiment, a process of determining the dissociation constant of a ligand can be performed in the presence of a second ligand. In accordance with this embodiment, the $^{15}$N-labeled target molecule is bound to that second ligand before exposing that target to the test compounds.

Binding or dissociation constants are measured by following the $^{15}$N/$^1$H chemical shifts of the protein as a function of ligand concentration. A known concentration ($[P]_0$) of the target molecule is mixed with a known concentration ($[L]_0$) of a previously identified ligand and the two-dimensional $^{15}$N/$^1$H correlation spectrum was acquired. From this spectrum, observed chemical shift values ($\delta_{obs}$) are obtained. The process is repeated for varying concentrations of the ligand to the point of saturation of the target molecule, when possible, in which case the limiting chemical shift value for saturation ($\delta_{sat}$) is measured.

In those situations where saturation of the target molecule is achieved, the dissociation constant for the binding of a particular ligand to the targer molecule is calculated using the formula:

$$K_D = \frac{([P]_0 - x)([L]_0 - x)}{x}$$

where $[P]_0$ is the total molar concentration of target molecule; $[L]_0$ is the total molar concentration of ligand; and x is the molar concentration of the bound species. The value of x is determined from the equation:

$$x = \frac{\delta_{obs} - \delta_{free}}{\Delta}$$

where $\delta_{free}$ is the chemical shift of the free species; $\delta_{obs}$ is the observed chemical shift; and $\Delta$ is the differenec between the limiting chemical shift value for saturation ($\delta_{sat}$) and the chemical shift value of the target molecule free of ligand ($\delta_{free}$).

The dissociation constant is then determined by varying its value until a best fit to the observed data is obtained using standard curve-fitting statistical methods. In the case where $\delta_{sat}$ is not directly known, both $K_D$ and $\delta_{sat}$ are varied and subjected to the same curve-fitting procedure.

The use of the process described above to determine the dissociation or binding affinity of various ligands to various target molecules is set forth hereinafter in Examples 2 and 3.

Preferred target molecules, means for generating spectra, and means for comparing spectra are the same as set forth above.

In its principal aspect, the present invention provides a process of designing new ligands that bind to a specific target molecule by linking together two or more molecules that bind to the target molecule.

The initial step in the design process is the identification of two or more ligands that bind to the specific target molecule. The identification of such ligands is done using two-dimensional $^{15}N/^{1}H$ NMR correlation spectroscopy as set forth above.

Once two or more ligands are identified as binding to the target molecule at different sites, a complex between the target molecule and ligands is formed. Where there are two ligands, that complex is a ternary complex. Quaternary and other complexes are formed where there are three or more ligands.

Complexes are formed by mixing the target molecule simultaneously or sequentially with the various ligands under circumstances that allow those ligands to bind the target. Means for determining those conditions are well known in the art.

Once that complex is formed, its three-dimensional structure is determined. Any means of determining three-dimensional structure can be used. Such methods are well known in the art. Exemplary and preferred methods are NMR and X-ray crystallography. The use of three-dimensional double- and triple resonance NMR to determine the three-dimensional structure of two ligands bound to the catalytic domain of stromelysin is set forth in detail hereinafter in Example 4.

An analysis of the three-dimensional structure reveals the spatial orientation of the ligands relative to each other as well as to the conformation of the target molecule. First, the spatial orientation of each ligand to the target molecule allows for identification of those portions of the ligand directly involved in binding (i.e., those portions interacting with the target binding site) and those portions of each ligand that project away from the binding site and which portions can be used in subsequent linking procedures.

Second, the spatial orientation data is used to map the positions of each ligand relative to each other. In other words, discrete distances between the spatially oriented ligands can be calculated.

Third, the spatial orientation data also defines the three-dimensional relationships amongst the ligands and the target. Thus, in addition to calculating the absolute distances between ligands, the angular orientations of those ligands can also be determined.

Knowledge of the spatial orientations of the ligands and target is then used to select linkers to link two or more ligands together into a single entity that contains all of the ligands. The design of the linkers is based on the distances and angular orientation needed to maintain each of the ligand portions of the single entity in proper orientation to the target.

The three-dimensional conformation of suitable linkers is well known or readily ascertainable by one of ordinary skill in the art. While it is theoretically possible to link two or more ligands together over any range of distance and three-dimensional projection, in practice certain limitations of distance and projection are preferred. In a preferred embodiment, ligands are separated by a distance of less than about 15 Angstroms (Å), more preferably less than about 10 Å and, even more preferably less than about 5 Å.

Once a suitable linker group is identified, the ligands are linked with that linker. Means for linking ligands are well known in the art and depend upon the chemical structure of the ligand, and the linking group itself. Ligands are linked to one another using those portions of the ligand not directly involved in binding to the target molecule.

A detailed description of the design of a drug that inhibits the proteolytic activity of stromelysin, which drug was designed using a process of the present invention is set forth hereinafter in Example 4.

The following Examples illustrate preferred embodiments of the present invention and are not limiting of the specification and claims in any way.

EXAMPLE 1

Preparation Of Uniformly $^{15}N$-labeled Target Molecules

A. Stromelysin

Human stromelysin is a 447-amino acid protein believed to be involved in proteolytic degradation of cartilage. Cartilage proteolysis is believed to result in degradative loss of joint cartilage and the resulting impairment of joint function observed in both osteoarthritis and rheumatoid arthritis. The protein possesses a series of domains including N-terminal latent and propetide domains, a C-terminal domain homologous with homopexin, and an internal catalytic domain.

Studies have shown that removal of the N-terminal prosequence of approximately eighty amino acids occurs to convert the proenzyme to the 45 kDa mature enzyme. Furthermore, studies have shown that the C-terminal homopexin homologous domain is not required for proper folding of the catalytic domain or for interaction with an inhibitor. (See, e.g., A. I. Marcy, *Biochemistry*, 30: 6476–6483 (1991). Thus, the 81–256 amino acid residue internal segment of stromelysin was selected as the protein fragment for use in identifying compounds which bind to and have the potential as acting as inhibitors of stromelysin.

To employ the method of the present invention, it was necessary to prepare the 81–256 fragment (SEQ ID NO:1) of stromelysin in which the peptide backbone was isotopically enriched with and $^{15}N$. This was done by inserting a plasmid which coded for the production of the protein fragment into an *E. coli* strain and growing the genetically-modified bacterial strain in a limiting culture medium enriched with $^{15}NH_4Cl$ and $^{13}C$-glucose.

The isotopically enriched protein fragment was isolated from the culture medium, purified, and subsequently used as the basis for evaluating the binding of test compounds. The procedures for these processes are described below.

Human skin fibroblasts (ATCC No. CRL 1507) were grown and induced using the procedure described by Clark et al., *Archiv. Biochem. and Biophys.*, 241: 36–45 (1985). Total RNA was isolated from 1 g of cells using a Promega RNAgents® Total RNA Isolation System Kit (Cat.# Z5110, Promega Corp., 2800 Woods Hollow Road, Madison, Wis. 53711-5399) following the manufacturer's instructions. A 1 μg portion of the RNA was heat-denatured at 80° C. for five minutes and then subjected to reverse transcriptase PCR using a GeneAmp® RNA PCR kit (Cat.# N808-0017, Applied Biosystems/Perkin-Elmer, 761 Main Avenue, Norwalk, Conn. 06859-0156) following the manufacturer's instructions.

Nested PCR was performed using first primers (A) GAAATGAAGAGTC TTCAA (SEQ ID NO:3) and (B) GCGTCCCAGGTTCTGGAG (SEQ ID NO:4) and thirty-five cycles of 94° C., two minutes; 45° C., two minutes; and 72° C. three minutes. This was followed by reamplification with internal primers (C) ATACCATGGCCTATCCAT TGGATGGAGC (SEQ ID NO:5) and (D) ATAGGATCCG-FAGGTCTCAGGGGA GTCAGG (SEQ ID NO:6) using thirty cycles under the same conditions described immediately above to generate a DNA coding for amino acid residues 1–256 of human stromelysin.

The PCR fragment was then cloned into PCR cloning vector pT7Blue(R) (Novagen, Inc., 597 Science Drive, Madison, Wis. 53711) according to the manufacturer's instructions. The resulting plasmid was cut with NcoI and BamHI and the stromelysin fragment was subcloned into the Novagen expression vector pET3d (Novagen, Inc., 597 Science Drive, Madison, Wis. 53711), again using the manufacturer's instructions.

A mature stromelysin expression construct coding for amino acid residues 81–256 plus an initiating methionine was generated from the 1–256 expression construct by PCR amplification. The resulting PCR fragment was first cloned into the Novagen pT7Blue(R) vector and then subcloned into the Novagen pET3d vector, using the manufacturer's instructions in the manner described above, to produce plasmid (pETST-83-256). This final plasmid is identical to that described by Qi-Zhuang et al., *Biochemistry*, 31: 11231–11235 (1992) with the exception that the present codes for a peptide sequence beginning two amino acids earlier, at position 81 in the sequence of human stromelysin.

Plasmid pETST-83-256 was transformed into *E. coli* strain BL21(DE3)/pLysS (Novagen, Inc., 597 Science Drive, Madison, Wis. 53711) in accordance with the manufacturer's instructions to generate an expression strain, BL21(DE3)/pLysS/pETST-255-1.

A preculture medium was prepared by dissolving 1.698 g of $Na_2HP_4.7H_2O$, 0.45 g of $KH_2PO_4$, 0.075 g NaCl, 0.150 g $^{15}NH_4Cl$, 0.300 13C-glucose, 300 μL of 1M aqueous $MgSO_4$ solution and 15 μL of aqueous $CaCl_2$ solution in 150 mL of deionized water.

The resulting solution of preculture medium was sterilized and transferred to a sterile 500 mL baffle flask. Immediately prior to inoculation of the preculture medium with the bacterial strain, 150 μL of a solution containing 34 mg/mL of chloramphenicol in 100% ethanol and 1.5 mL of a solution containing 20 mg/mL of ampicillin were added to the flask contents.

The flask contents were then inoculated with 1 mL of glycerol stock of genetically-modified *E. Coli*, strain BL21 (DE3)/pLysS/pETST-255-1. The flask contents were shaken (225 rpm) at 37° C. until an optical density of 0.65 was observed.

A fermentation nutrient medium was prepared by dissolving 113.28 g of $Na_2HP_4.7H_2O$, 30 g of $KH_2PO_4$, 5 g NaCl and 10 mL of 1% DF-60 antifoam agent in 9604 mL of deionized water. This solution was placed in a New Brunswick Scientific Micros Fermenter (Edison, N.J.) and sterilized at 121° C. for 40 minutes.

Immediately prior to inoculation of the fermentation medium, the following pre-sterilized components were added to the fermentation vessel contents: 100 mL of a 10% aqueous solution of $^{15}NH_4Cl$, 100 mL of a 10% aqueous solution of $^{13}C$-glucose, 20 mL of an aqueous 1M solution of $MgSO_4$, 1 mL of an aqueous 1M $CaCl_2$ solution, 5 mL of an aqueous solution of thiamin hydrochloride (10 mg/mL), 10 mL of a solution containing 34 mg/mL of chloramphenicol in 100% ethanol and 1.9 g of ampicillin dissolved in the chloramphenicol solution. The pH of the resulting solution was adjusted to pH 7.00 by the addition of an aqueous solution of 4N $H_2SO_4$.

The preculture of *E. Coli*, strain BL21(DE3)/pLysS/pETST-255-1, from the shake-flask scale procedure described above was added to the fermentor contents and cell growth was allowed to proceed until an optical density of 0.48 was achieved. During this process, the fermenter contents were automatically maintained at pH 7.0 by the addition of 4N $H_2SO_4$ or 4N KOH as needed. The dissolved oxygen content of the fermenter contents was maintained above 55% air saturation through a cascaded loop which increased agitation speed when the dissolved oxygen content dropped below 55%. Air was fed to the fermenter contents at 7 standard liters per minute (SLPM) and the culture temperature was maintained at 37° C. throughout the process.

The cells were harvested by centrifugation at 17,000×g for 10 minutes at 4° C. and the resulting cell pellets were collected and stored at –85° C. The wet cell yield was 3.5 g/L. Analysis of the soluble and insoluble fractions of cell lysates by sodium dodecyl sulfate polyacrylamide gel electrophoresis (SDS-PAGE) revealed that approximately 50% of the $^{15}N$-stromelysin was found in the soluble phase.

The isotopically-labeled stromelysin fragment prepared as described above was purified employing a modification of the technique described by Ye et al., *Biochemistry*, 31: 11231–11235 (1992).

The harvested cells were suspended in 20 mM Tris-HCl buffer (pH 8.0) sodium azide solution containing 1 mM $MgCl_2$, 0.5 mM $ZnCl_2$, 25 units/mL of Benzonase® enzyme, and an inhibitor mixture made up of 4-(2-aminoethyl)-benzenesulfonyl fluoride ("AEBSF"), Leupepting®, Aprotining®, and Pepstating® (all at concentrations of 1 μg/mL. AEBSF, Leupeptin®, Aprotinin®, and Pepstatin® are available from American International Chemical, 17 Strathmore Road, Natick, Mass. 01760.)

The resulting mixture was gently stirred for one hour and then cooled to 4° C. The cells were then sonically disrupted using a 50% duty cycle. The resulting lysate was centrifuged at 14,000 rpm for 30 minutes and the pellet of insoluble fraction frozen at –80° C. for subsequent processing (see below).

Solid ammonium sulfate was added to the supernatant to the point of 20% of saturation and the resulting solution loaded onto a 700 mL phenyl sepharose fast flow ("Q-Sepharose FF") column (Pharmacia Biotech., 800 Centennial Ave., P.O. Box 1327, Piscataway, N.J. 08855). Prior to loading, the sepharose column was equilibrated with 50 mM Tris-HCl buffer (pH 7.6 at 4° C.), 5 mM $CaCl_2$, and 1M $(NH_4)_2SO_4$. The loaded column was eluted with a linear gradient of decreasing concentrations of aqueous $(NH_4)_2SO_4$ (from 1 down to 0M) and increasing concentrations of aqueous $CaCl_2$ (from 5 to 20 mM) in Tris-HCl buffer at pH 7.6.

The active fractions of eluate were collected and concentrated in an Amicon stirred cell (Amicon, Inc., 72 Cherry Hill Drive, Beverly, Mass. 01915). The concentrated sample was dialyzed overnight in the starting buffer used with the Q-Sepharose FF column, 50 mM Tris-HCl (pH 8.2 at 4° C.) with 10 mM $CaCl_2$.

The dialyzed sample was then loaded on the Q-Sepharose FF column and eluted with a linear gradient comprising the starting buffer and 200 mM NaCl. The purified soluble fraction of the isotopically-labeled stromelysin fragment was concentrated and stored at 4° C.

The pellet was solubilized in 8M guanidine-HCl. The solution was centrifuged for 20 minutes at 20,000 rpm and the supernatant was added dropwise to a folding buffer comprising 50 mM Tris-HCl (pH 7.6), 10 mM $CaCl_2$ 0.5 mM $ZnCl_2$ and the inhibitor cocktail of AEBSF, Leupeptin®, Aprotinin®, and Pepstatin® (all at concentrations of 1 μg/mL). The volume of folding buffer was ten times that of the supernatant. The mixture of supernatant and folding buffer was centrifuged at 20,000 rpm for 30 minutes.

The supernatant from this centrifugation was stored at 4° C. and the pellet was subjected twice to the steps described above of solubilization in guanidine-HCl, refolding in buffer, and centrifugation. The final supernatants from each of the three centrifugations were combined and solid ammonium sulfate was added to the point of 20% saturation. The resulting solution thus derived from the insoluble fraction was subjected to purification on phenyl Sepharose and Q-Sepharose as described above for the soluble fraction.

The purified soluble and insoluble fractions were combined to produce about 1.8 mg of purified isotopically-labeled stromelysin 81–256 fragment per gram of original cell paste.

B. Human papillomavirus (HPV) E2 Inhibitors

The papillomaviruses are a family of small DNA viruses that cause genital warts and cervical carcinomas. The E2 protein of HPV regulates viral transcription and is required for viral replication. Thus, molecules that block the binding of E2 to DNA may be useful therapeutic agents against HPV. The protein rather than the DNA was chosen as a target, because it is expected that agents with greater selectivity would be found that bind to the protein rather than the DNA.

The DNA-binding domain of human papillomavirus E2 was cloned from the full length DNA that codes for E2 using PCR and overexpressed in bacteria using the T7 expression system. Uniformly $^{15}$N-labeled protein was isolated from bacteria grown on a minimal medium containing $^{15}$N-labeled protein was isolated from bacteria grown on a minimal medium containing $^{15}$N-labeled ammonium chloride. The protein was purified from the bacterial cell lysate using an S-sepharose FastFlow column pre-equilibrated with buffer (50 mM Tris, 100 mM NaCl, 1 mM EDTA, pH=8.3).

The protein was eluted with a linear gradient of 100–500 mM NaCl in buffer, pooled, and applied to a Mono-S column at a pH=7.0. The protein was eluted with a salt gradient (100–500 mM), concentrated to 0.3 mM, and exchanged into a TRIS (50 mM, pH=7.0 buffered $H_2O/D_2O$ (9/1) solution containing sodium azide (0.5%).

C. RAF

Uniformly $^{15}$N-labeled Ras-binding domain of the RAF protein was prepared as described in Emerson et al., *Biochemisty*, 34 (21): 6911–6918 (1995).

D. FKBP

Uniformly $^{15}$N-labeled recombinant human FK binding protein (FKBP) was prepared as described in Logan et al., *J. Mol. Biol.*, 236: 637–648 (1994).

EXAMPLE 2

Screening Compounds Using Two-Dimensional $^{15}$N/$^{1}$H NMR Correlation Spectral Analysis The catalytic domain of stromelysin was prepared in accordance with the procedures of Example 1. The protein solutions used in the screening assay contained the uniformly $^{15}$N-labeled catalytic domain of stromelysin (0.3 mM), acetohydroxamic acid (500 mM), $CaCl_2$ (20 mM), and sodium azide (0.5%) in a $H_2O/D_2O$ (9/1) TRIS buffered solution (50 mM, pH=7.0).

Two-dimensional $^{15}$N/$^{1}$H NMR spectra were generated at 29° C. on a Bruker AMX500 NMR spectrometer equipped with a triple resonance probe and Bruker sample changer. The $^{15}$N/$^{1}$H HSQC spectra were acquired as 80×1024 complex points using sweep widths of 2000 Hz ($^{15}$N, t$^{1}$) and 8333 Hz ($^{1}$H, t2). A delay of 1 second between scans and 8 scans per free induction decay(fid) were employed in the data collection. All NMR spectra were processed and analyzed on Silicon Graphics computers using in-house-written software.

A first two-dimensional $^{15}$N/$^{1}$H NMR correlation spectrum was acquired for the $^{15}$N-labeled stromelysin target molecule as described above. The stromelysin target was then exposed to a database of test compounds. Stock solutions of the compounds were made at 100 mM and 1M. In addition, a combination library was prepared that contained 8–10 compounds per sample at a concentration of 100 mM for each compound.

The pH of the 1M stock solution was adjusted with acetic acid and ethanolamine so that no pH change was observed upon a $^{1}/_{10}$ dilution with a 100 mM phosphate buffered solution (pH=7.0). It is important to adjust the pH, because small changes in pH can alter the chemical shifts of the biomolecules and complicate the interpretation of the NMR data.

The compounds in the database were selected on the basis of size (molecular weight=100–300) and molecular diversity. The molecules in the collection had different shapes (e.g., flat aromatic rings(s), puckered aliphatic rings(s), straight and branched chain aliphatics with single, double, or triple bonds) and diverse functional groups (e.g., carboxylic acids, esters, ethers, amines, aldehydes, ketones, and various heterocyclic rings) for maximizing the possibility of discovering compound that interact with widely diverse binding sites.

The NMR samples were prepared by adding 4 $\mu$l of the DMSO stock solution of the compound mixtures that contained each compound at a concentration of 100 mM to 0.4 ml $H_2O/D_2O$ (9/1) buffered solution of the uniformly $^{15}$N-labeled protein. The final concentration of each of the compounds in the NMR sample was about 1 mM.

In an initial screen, two compounds were found that bind to the catalytic domain of stromelysin. Both of these compounds contain a biaryl moiety. Based on these initial hits, structurally similar compounds were tested against stromelysin. The structure of those biaryl compounds is represented by the structure I, below. (See Table 1 for definitions of $R_1$–$R_3$ and $A_1$–$A_3$).

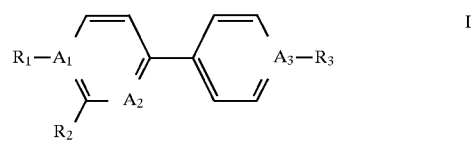

In the second round of screening, binding was assayed both in the absence and in the presence of saturating amounts of acetohydroxamic acid (500 mM).

Figure 4:
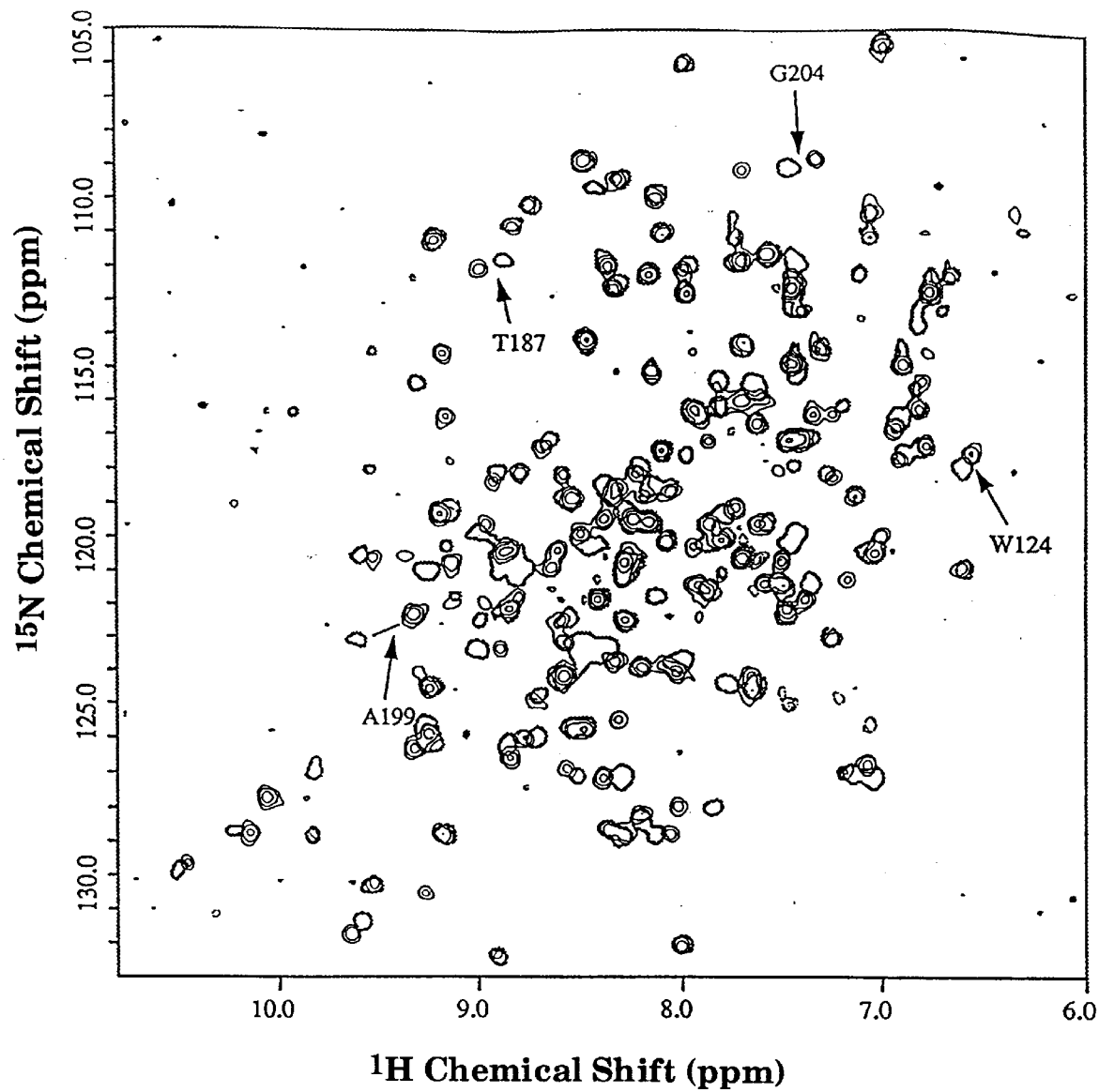
FIG. 4 shows $^{15}N/^1H$ correlation spectra of the catalytic domain of uniformly $^{15}N$-labeled stromelysin before (thin multiple contours) and after (thick single contours) addition of a test compound. The final concentration of compound was 1.0 mM. The spectra (80 complex points, 8 scans/fid) were acquired on a 0.3 mM sample of SCD in 20 mM TRIS (pH 7.0), 20 mM $CaCl_2$ and 10% $D_2O$. Selected residues that show significant changes upon binding are indicated.

Many of the biaryl compounds were found to bind the catalytic domain of stromelysin. FIG. 4 shows a representative two-dimensional $^{15}$N/$^{1}$H NMR correlation spectrum before and after exposure of stromelysin to a biaryl test compound. It can be seen from FIG. 4 that the compound caused chemical shifts of $^{15}$N-sites such as those designated W124, T187, A199 and G204.

Figure 9:
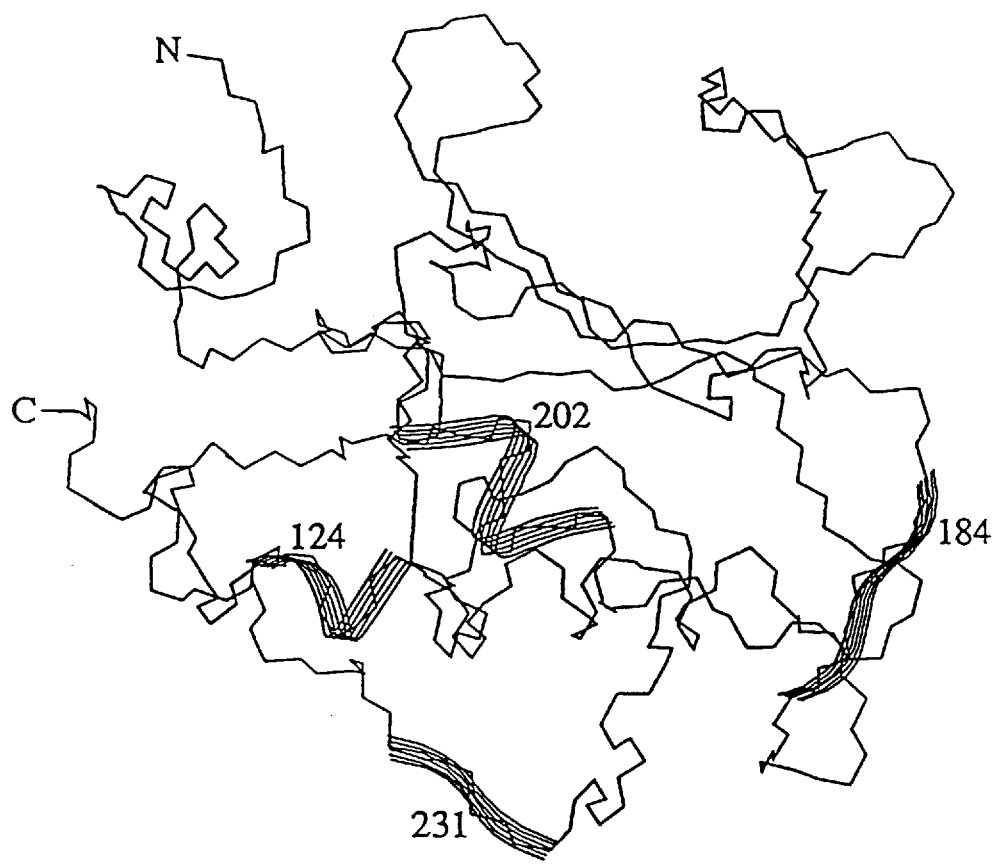
FIG. 9 shows a depiction of the NMR-derived structure of the catalytic domain of stromelysin. The N- and C-termini are indicated. Shown in ribbons are the residues which exhibit significant chemical shift changes ($\Delta\delta(^1H)>0.04$ ppm; $\Delta\delta(^{15}N)>0.1$ ppm) upon binding to a test compound. These either form part of the S1' binding site or are spatially proximal to this site. Selected residues are numbered for aid in visualization.

These sites correspond to a tryptophan (Trp) residue at position 124, a threonine (Thr) at position 187, an alanine (Ala) at position 199, and a glycine (Gly) at position 204 of SEQ ID NO. 1. FIG. 9 shows the correlation between the NMR binding data and a view of the NMR-derived three-dimensional structure of the catalytic domain of stromelysin. The ability to locate the specific binding site of a particular ligand is an advantage of the present invention.

Some compounds only bound to stromelysin in the presence of hydroxamic acid. Thus, the binding affinity of some compounds was enhanced in the presence of the hydroxamic acid (i.e. cooperative). These results exemplify another important capability of the present screening assay: the ability to identify compounds that bind to the protein in the presence of other molecules.

Various biaryl compounds of structure I were tested for binding to stromelysin at differing concentrations. The $^{15}$N/$^1$H spectra generated at each concentration were evaluated to quantify differences in the spectra as a function of compound concentration. A binding or dissociation constant ($K_D$) was calculated, using standard procedures well known in the art, from those differences. The result of this study are shown in Table 1. The values for R1–R3 and A1–A3 in Table 1 refer to the corresponding positions in the structure I, above.

TABLE 1

| Compound No. | $R_1$ | $R_2$ | $R_3$ | $A_1$ | $A_2$ | $A_3$ | $K_D$ (mM) |
|---|---|---|---|---|---|---|---|
| 1 | H | OH | H | C | C | C | 1.1 |
| 2 | CH$_2$OH | H | H | C | C | C | 3.2 |
| 3 | Br | H | OH | C | C | C | 1.3 |
| 4 | H | H | H | N | N | C | 1.6 |
| 5 | CHO | H | H | C | C | C | 1.7 |
| 6 | OCH$_3$ | NH$_2$ | H | C | C | C | 0.4 |
| 7 | H | H | H | N | C | C | 0.2 |
| 8 | OCOCH$_3$ | H | H | C | C | C | 0.3 |
| 9 | OH | H | OH | C | C | C | 0.01 |
| 10 | H | H | H | N | C | N | 0.4 |
| 11 | OH | H | H | C | C | C | 0.3 |
| 12 | OH | H | CN | C | C | C | 0.01 |

The data in Table 1 show the utility of a process of the present invention in determining dissociation or binding constants between a ligand and a target molecule Another advantage of an NMR screening assay of the present invention is the ability to correlate observed chemical shifts from the two-dimensional $^{15}$N/$^1$H NMR correlation spectra-with other spectra or projections of target molecule configuration. The results of a representative such correlation are shown in FIG. 9, which depicts regions within the polypeptide at which binding with the substrate molecule is most likely occurring. In this Figure, the apparent binding regions in stromelysin are shown for Compound 1 (from Table 1).

Compounds from the database were screened in a similar manner for binding to the DNA-binding domain of the E2 protein. Those compounds had the structure II below, where $R_1$–$R_4$ and A are defined in Table 2.

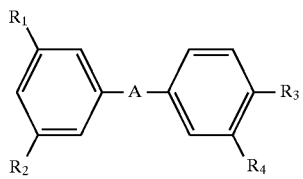

II

NMR experiments were performed at 29° C. on a Bruker AMX500 NMR spectrometer equipped with a triple resonance probe and Bruker sample changer. The $^{15}$N-/$^1$H HSQC spectra were acquired as 80×1024 complex points using sweep widths of 2000 Hz ($^{15}$N,t$_1$) and 8333 Hz ($^1$H, t$_2$). A delay of 1 second between scans and 4 scans per free induction decay were employed in the data collection. All NMR spectra were processed and analyzed on Silicon Graphics computers.

Figure 3:
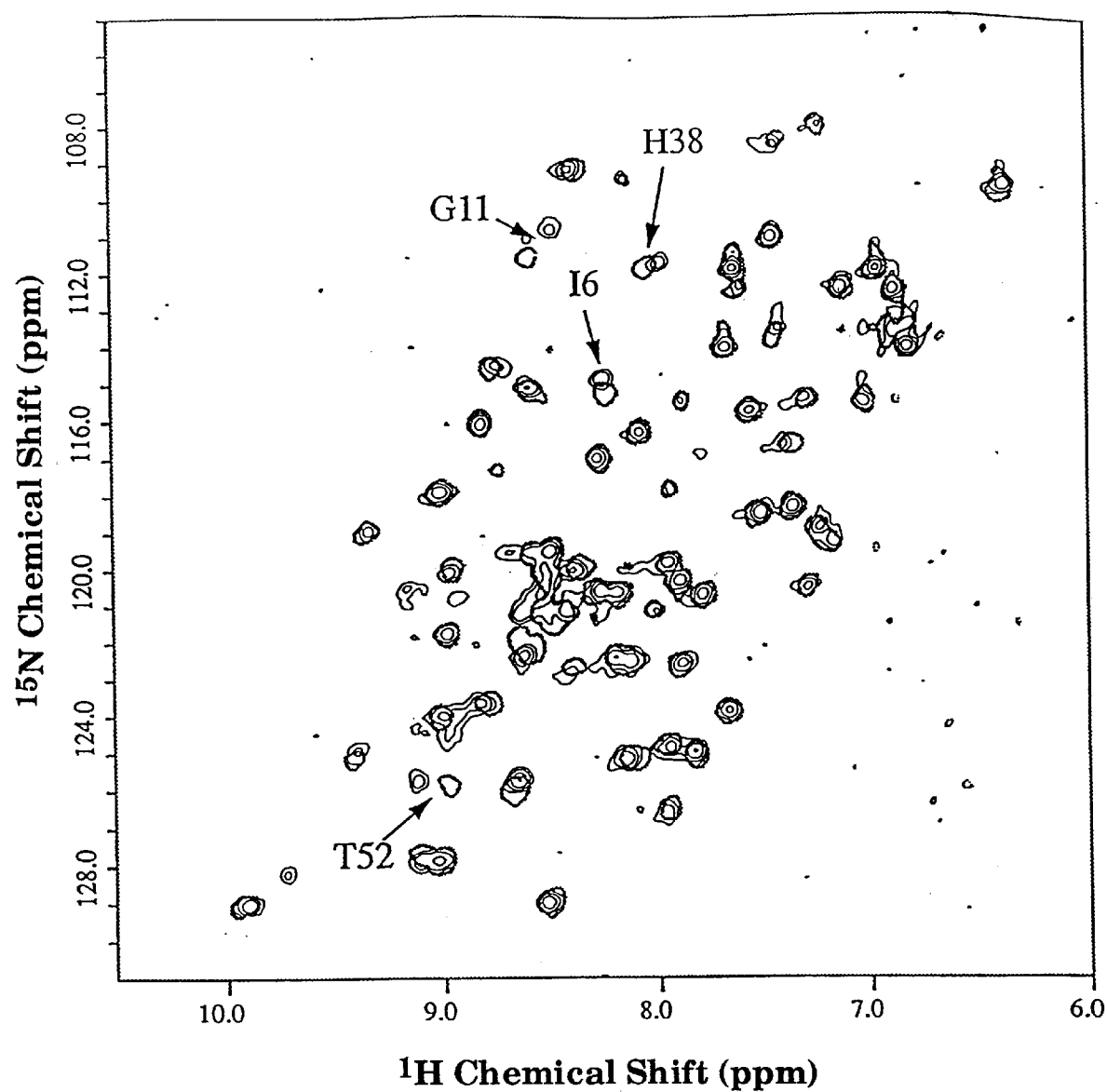
FIG. 3 shows $^{15}N/^1H$ correlation spectra of the DNA binding domain of uniformly $^{15}N$-labeled human papillomavirus E2 before (thin multiple contours) and after (thick single contours) addition of a second test compound. The final concentration of compound was 1.0 mM. All other conditions are as stated in FIG. 1. Selected residues that show significant changes upon binding are indicated.

FIGS. 2 and 3 show representative two-dimensional $^{15}$N/$^1$H NMR is correlation spectra before and after exposure of the DNA-binding domain of E2 to a first and second test compound, respectively.

It can be seen from FIG. 2 that the first test compound caused chemical shifts of $^{15}$N-sites such as those designated I15, Y21, R22 and L23. Those sites correspond to an isoleucine (Ile) residue at position 15, a tyrosine residue (Tyr) at position 21, an arginine (Arg residue at position 22 and a leucine (Leu) residue at position 23 of SEQ ID NO. 6.

It can be seen from FIG. 3 that the second test compound caused chemical shifts in the particular $^{15}$N-sites designated I6, G11, H38, and T52. Those sites correspond to an isoleucine (Ile) residue at position 6, a glycine (Gly) residue at position 11, a histidine (His) residue at position 38 and a threonine (Thr) at position 52 of SEQ ID NO. 6.

Figure 7:
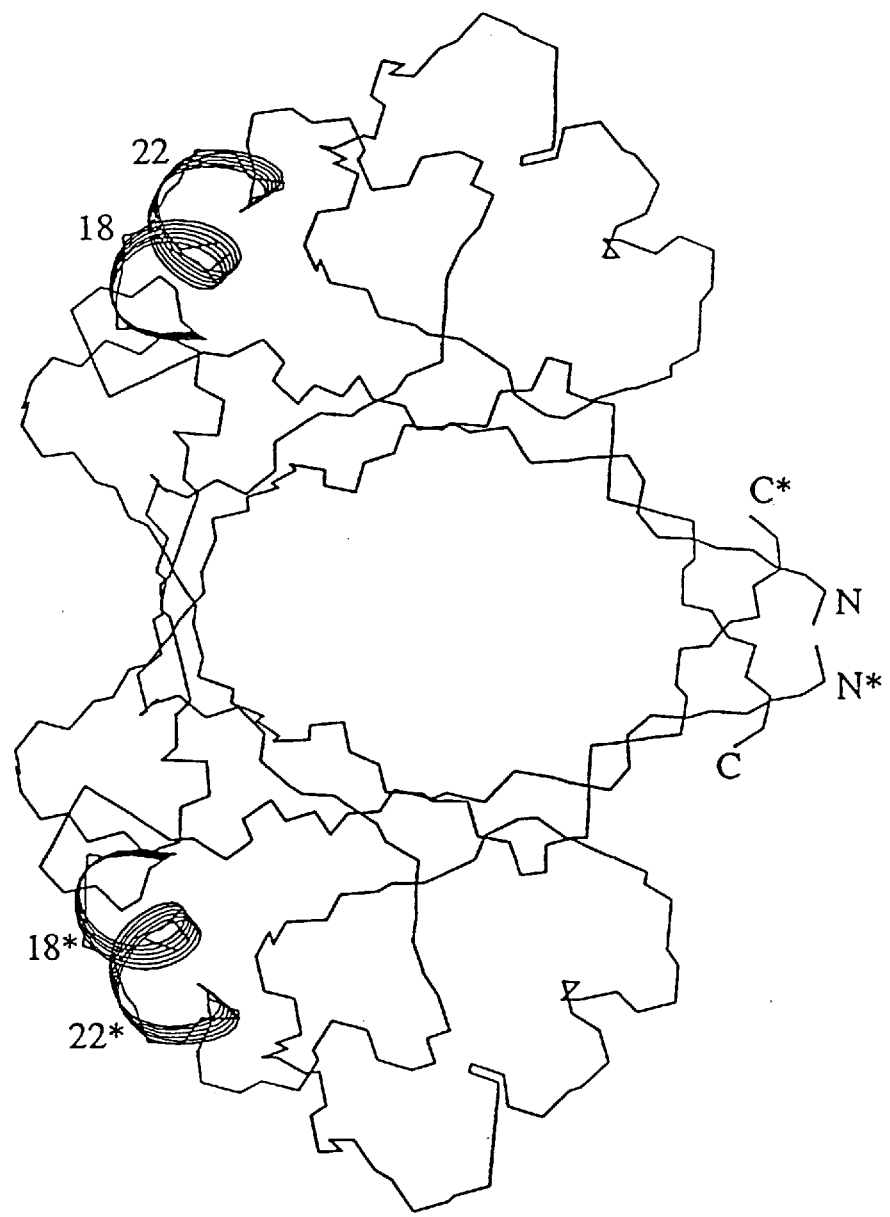
FIG. 7 shows a first depiction of the NMR-derived structure of the DNA-binding domain of E2. The two monomers of the symmetric dimer are oriented in a top-bottom fashion, and the N- and C-termini of each monomer are indicated (N and C for one monomer, N* and C* for the other). Shown in ribbons are the residues which exhibit significant chemical shift changes ($\Delta\delta(^1H)>0.04$ ppm; $\Delta\delta(^{15}N)>0.1$ ppm) upon binding to a first test compound. These residues correspond to the DNA-recognition helix of E2. Selected residues are numbered for aid in visualization.
Figure 8:
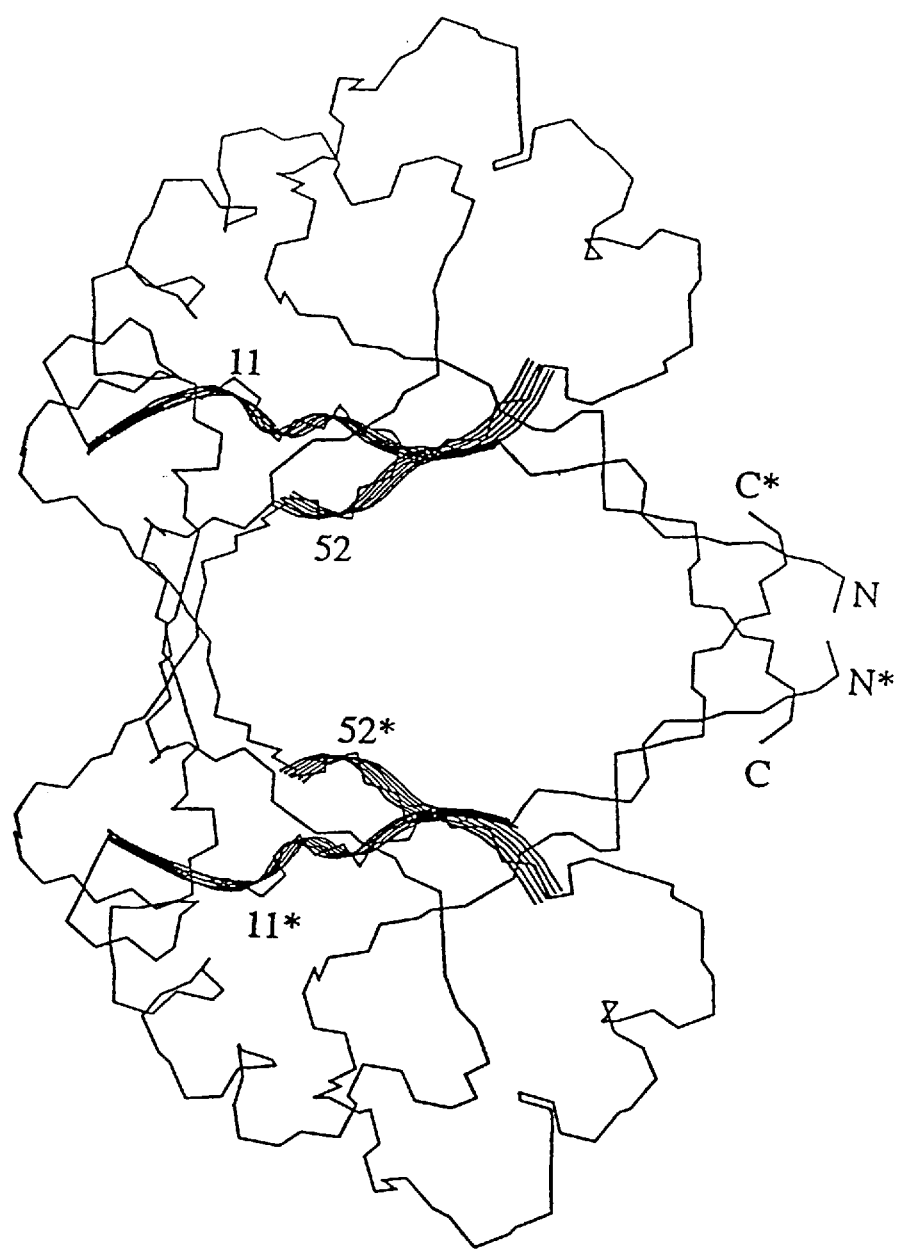
FIG. 8 shows a second depiction of the NMR-derived structure of the DNA-binding domain of E2. The two monomers of the symmetric dimer are oriented in a top-bottom fashion, and the N- and C-termini of each monomer are indicated (N and C for one monomer, N* and C* for the other). Shown in ribbons are the residues which exhibit significant chemical shift changes ($\Delta\delta(^1H)>0.04$ ppm; $\Delta\delta(^{15}N)>0.1$ ppm) upon binding to a second test compound. These residues are located primarily in the dimer interface region. Selected residues are numbered for aid in visualization.

FIGS. 7 and 8 show the correlation between those NMR binding data and a view of the NMR-derived three-dimensional structure of the DNA-binding domain of E2.

Several structurally similar compounds caused chemical shift changes of the protein signals when screened at a concentration of 1 mM. Two distinct sets of amide resonances were found to change upon the addition of the compounds: one set of signals corresponding to amides located in the β-barrel formed between the two monomers and a second set corresponding to amides located near the DNA-binding site.

For example, compounds containing two phenyl rings with a carboxylic acid attached to the carbon linking the two rings only caused chemical shift changes to the amides in the DNA-binding site. In contrast, benzophenones and phenoxyphenyl-containing compounds only bound to the β-barrel. Other compounds caused chemical shift changes of both sets of signals but shifted the signals in each set by different amounts, suggesting the presence of two distinct binding sites.

By monitoring the chemical shift changes as a function of ligand concentration, binding constants for the two binding sites were also measured. The results of those studies are summarized below in Table 2.

TABLE 2

| Comp. No. | A | $R_1$ | $R_2$ | $R_3$ | $R_4$ | DNA $K_D$ (mM) | β-barrel $K_D$ (mM) | Filter binding assay |
|---|---|---|---|---|---|---|---|---|
| 13 | CO | H | H | H | OH | >50 | 0.6 | − |
| 14 | O | H | H | H | CH$_2$OH | >50 | 2.0 | − |
| 15 | —$^a$ | H | H | COO | H | 2.0 | >50 | + |
| 16 | —$^a$ | Cl | Cl | COO | H | 0.1 | >50 | + |
| 17 | —$^a$ | H | H | CH$_2$COO | H | 4.2 | 4.9 | + |
| 18 | —$^a$ | H | H | CH=CHCOO | H | 1.2 | 6.2 | + |

TABLE 2-continued

| Comp. No. | A | $R_1$ | $R_2$ | $R_3$ | $R_4$ | DNA $K_D$ (mM) | β-barrel $K_D$ (mM) | Filter binding assay |
|---|---|---|---|---|---|---|---|---|
| 19 | O | H | H | $CH_2CH_2CH(CH_3)$—$CH_2COO$ | H | 0.5 | 0.2 | + |
| 20 | O | H | H | $COCH_2CH_2COO$ | H | 2.7 | 4.8 | + |

[a] a dash (—) for A indicates no atom (i.e. byphenyl linkage)

Figure 5:
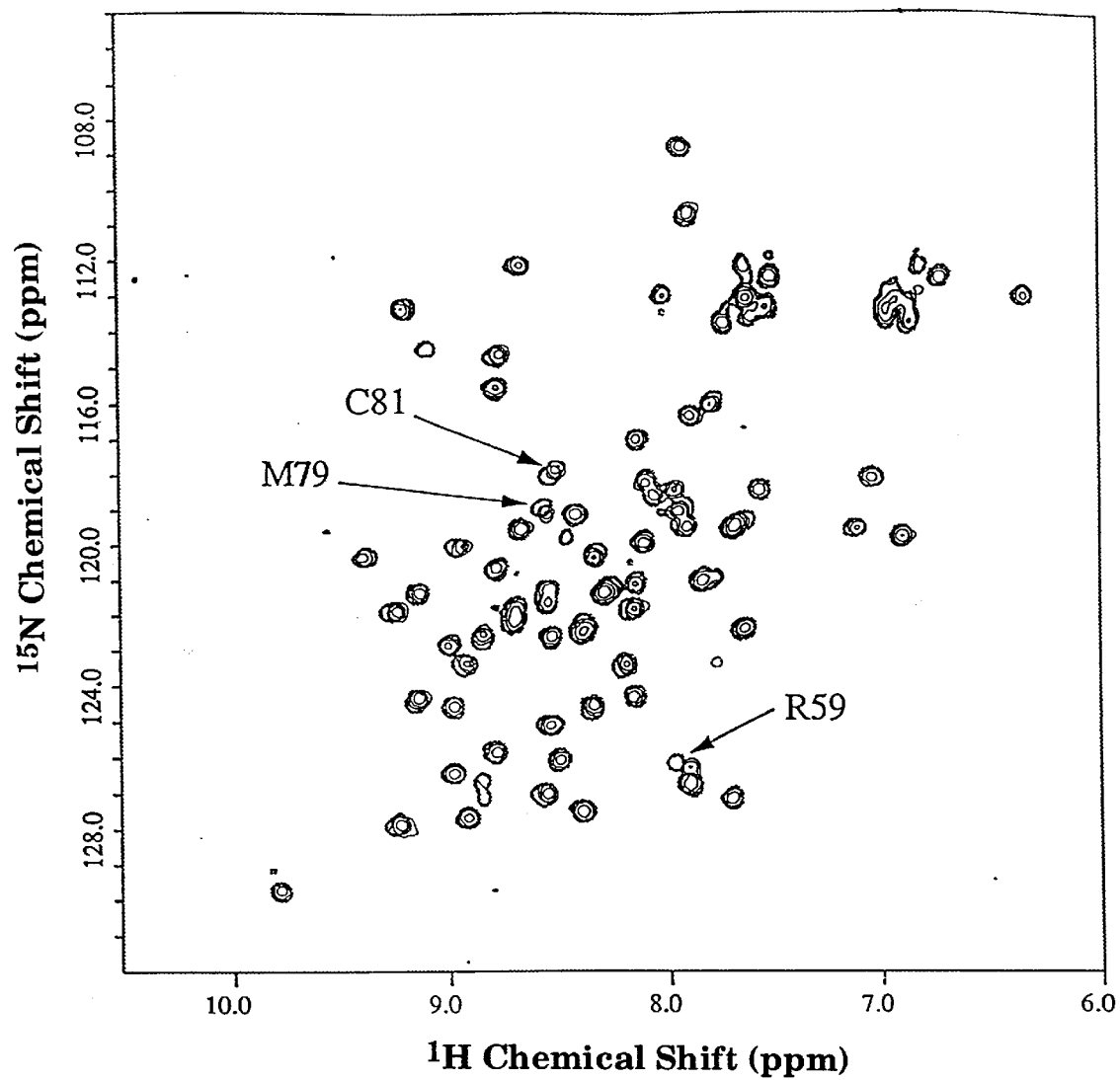
FIG. 5 shows $^{15}N/^1H$ correlation spectra of the Ras-binding domain of uniformly $^{15}N$-labeled RAF peptide (residues 55–132) before (thin multiple contours) and after (thick single contours) addition of a test compound. The final concentration of compound was 1.0 mM. The spectra (80 complex points, 8 scans/fid) were acquired on a 0.3 mM sample of the RAF fragment in 20 mM phosphate (pH 7.0), 10 mM DTT and 10% $D_2O$. Selected residues that show significant changes upon binding are indicated.

Uniformly $^{15}$N-labeled Ras-binding domain of the RAF protein was prepared as described in Example 1 and screened using two-dimensional $^{15}$N/$^1$H NMR correlation spectral analysis in accordance with the NMR procedures described above. The results of a representative study are shown in FIG. 5, which depicts two-dimensional $^{15}$N/$^1$H NMR correlation spectra both before and after exposure to a test compound.

Figure 6:
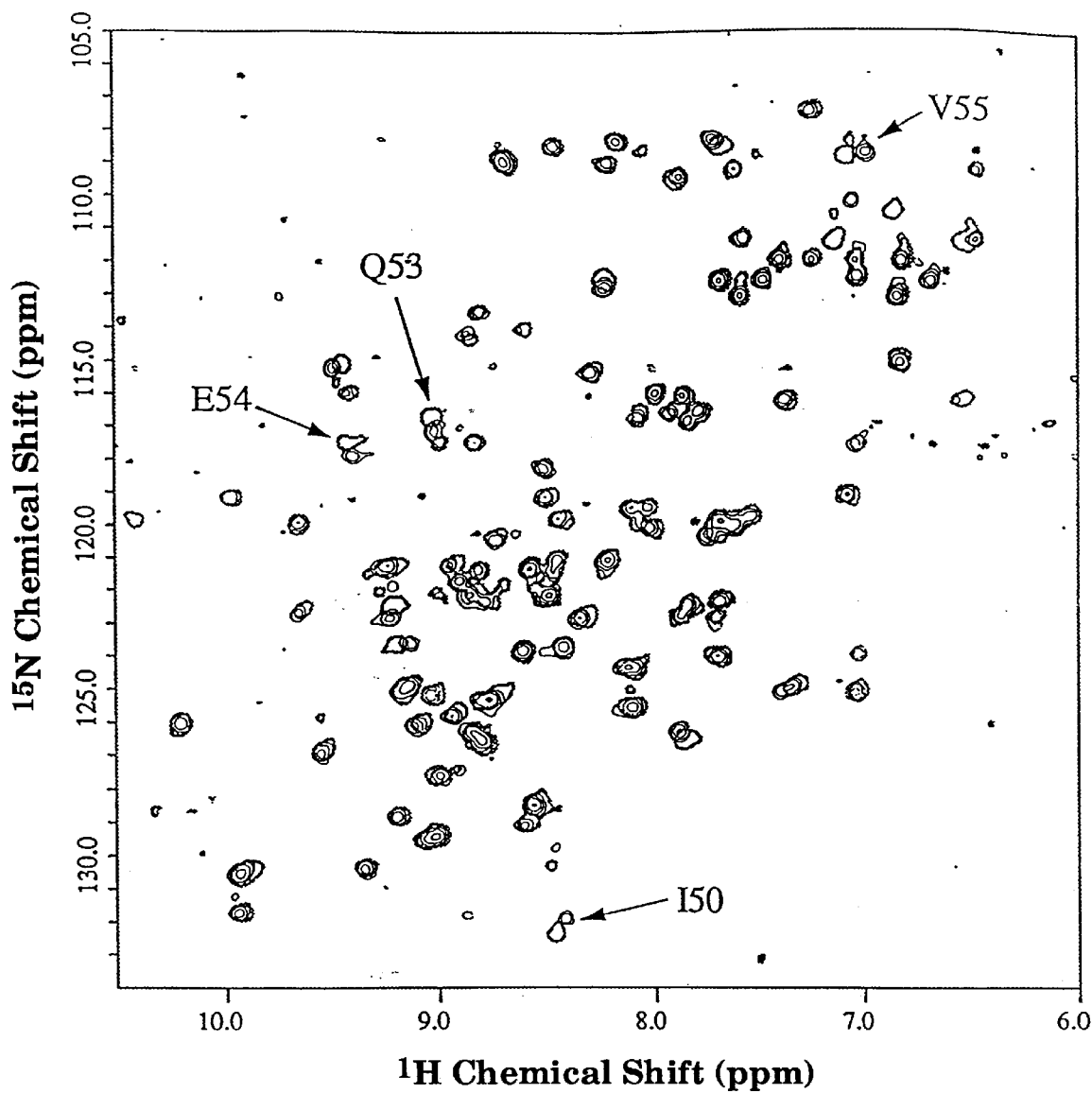
FIG. 6 shows $^{15}N/^1H$ correlation spectra of uniformly $^{15}N$-labeled FKBP before (thin multiple contours) and after (thick single contours) addition of a test compound. The final concentration of compound was 1.0 mM. The spectra (80 complex points, 4 scans/fid) was acquired on a 0.3 mM sample of FKBP in 50 mM phosphate (pH 6.5), 100 mM NaCl and 10% $D_2O$. Selected residues that show significant changes upon binding are indicated.

Uniformly $^{15}$N-labeled FKBP was prepared as described in Example 1 and screened using two-dimensional $^{15}$N/$^1$H NMR correlation spectral analysis in accordance with the NMR procedures described above. The results of a representative study are shown in FIG. 6, which depicts two-dimensional $^{15}$N/$^1$H NMR correlation spectra both before and after exposure to a test compound.

EXAMPLE 3

Comparison of NMR, Enzymatic, Filter Binding and Gel Shift Screening Assays

Studies were performed to compare binding constants of ligands to various biomolecules, determined by the NMR method of the present invention, to similar results obtained from prior art methods.

In a first study, binding constants were determined, both by the NMR method of the present invention, and by a prior art enzymatic assay. The target molecule was the catalytic domain of stromelysin prepared in accordance with the procedures of Example 1. The NMR binding constants, $K_D$, were derived using two-dimensional $^{15}$N/$^1$H NMR correlation spectroscopy as described in Example 2. The $K_D$ values so obtained were compared to an inhibition constant $K_I$ as determined in an enzymatic assay.

The enzymatic assay measured the rate of cleavage of a fluorogenic substrate by following the fluorescence increase upon peptide cleavage which causes a separation between the fluorophore and quencher. Enzymatic activity was measured using a matrix of different concentrations of acetohydroxamic acid and biaryl compounds. The assay is a modification of the method described by H. Weingarten, et al in *Anal. Biochem.*, 147: 437–440 (1985) employing the fluorogenic substrate properties described by E. Matayoshi, et al in *Science*: 247: 954–958 (1990).

Eight acetohydroxamic acid concentrations were used ranging from 0.0 to 1.0M, and six compound concentrations were used, resulting in a total of 48 points. Individual compound concentration varied due to solubility and potency.

All NMR measurements were performed in the presence of 500 mM acetohydroxamic acid, except for the titration of acetohydroxamic acid itself. Dissociation constants were obtained from the dependence of the observed chemical shift changes upon added ligand. Inhibition constants were then obtained from the inhibition data using standard procedures.

The results of these studies are summarized below in Table 3, which shows the comparison of NMR-derived dissociation constants ($K_D$) with inhibition constants measured in the enzyme assay ($K_I$) using a fluorogenic substrate.

TABLE 3

| Compound No. | NMR $K_D$ (mM) | Assay $K_I$ (mM) |
|---|---|---|
| 4 | 1.6 | 7.4 |
| 7 | 0.17 | 0.32 |
| 9 | 0.16 | 0.70 |
| 10 | 0.40 | 1.8 |
| 12 | 0.02 | 0.11 |
| Acetohydroxamic acid | 17.0 | 21.1 |

The data in Table 3 show that a NMR process of the present invention provides a rapid, efficient and accurate way of determining dissociation or binding constants of ligands to target biomolecules. Comparison of the binding constants determined by the two methods result in the same ranking of potencies of the compounds tested. That is, while the values for a given substrate as determined by the two methods are not equal, they are proportional to one another.

In a second study, the results for binding of the DNA-binding domain of E2 to its target DNA were obtained by prior art methods and compared with results obtained by the method of the present invention. The target was the DNA-binding domain of E2, prepared in accordance with the procedures of Example 1. NMR screening assays and NMR processes for determining ligand dissociation constants were performed as set forth above in Example 2.

The binding constant from the NMR process was compared to the results of a physical, filter binding assay that measured binding of DNA to the target. The high-throughput filter binding assay was performed using E2, prepared according to Example 2 above. The $^{33}$P-labeled DNA construct comprised a 10,329 base pair plasmid formed by inserting the HPV-11 genome, containing three high affinity and one low affinity E2 binding sites, into the PSP-65 plasmid (Promega, Madison, Wis.).

The binding affinities at the different sites as determined by NMR were compared for a subset of the compounds to the inhibition of E2 binding to DNA as measured in the filter binding assay. As shown in Table 2 above, the activities determined in the filter binding assay correlated closely with the binding affinities calculated from the amides of the DNA-binding site but not to the affinities measured for the β-barrel site. This is consistent with the relative locations of each site.

In an alternative study, a comparison of the NMR-determined binding results was made with similar results obtained by a prior art gel-shift assay using techniques well known in the art. The gel-shift assay was performed using a GST fusion protein which contained full length E2 and a $^{33}$P-labeled 62 base pair DNA fragment containing two E2 binding sites.

The method identified numerous compounds which gave positive results in the gel-shift assay. Some of these positive results, however, were believed to be due to binding to the DNA, since in these cases, no binding to the E2 protein was observed using the NMR method of this invention. These compounds were shown to indeed bind to DNA rather than to E2, as evidenced by changes in the chemical shifts of the DNA rather than the protein upon the addition of the compounds. These data show that yet another advantage of the present invention is the ability to minimize the occurrence of false positives.

EXAMPLE 4

Design of a potent, non-peptide inhibitor of stromelysin

Studies were performed to design new ligands that bound to the catalytic domain of stromelysin. Because stromelysin undergoes autolysis, an inhibitor was sought to block the degradation of stromelysin. That inhibitor would facilitate the screening of other potential ligands that bind to other sites on the enzyme.

The criteria used in selecting compounds in the screening for other binding sites was based primarily on the size of the ligand. The smallest ligand was sought that had enough solubility to saturate (>98% occupancy of enzyme) and inhibit the enzyme.

The cloning, expression, and purification of the catalytic domain of stromelysin was accomplished using the procedures set forth in Example 1. An initial step in the design of the new ligand was the identification of a first ligand that bound to the stromelysin target Such identification was carried out in accordance with a two-dimensional $^{15}$N/$^{1}$H NMR correlation screening process as disclosed above.

A variety of hydroxamic acids of the general formula R—(CO)NHOH were screened for binding to stromelysin using the procedures set forth in Example 2. Of the compounds tested, acetohydroxamic acid [CH3(CO)NHOH] best satisfied the selection criteria: it had a binding affinity for stromelysin of 17 mM and had good water solubility. At a concentration of 500 mM, acetohydroxamic acid inhibited the degradation of the enzyme, allowing the screening of other potential ligands.

The second step in the design process was the identification of a second ligand that bound to the target stromelysin at a site different from the binding site of acetohydroxamic acid. This was accomplished by screening compounds for their ability to bind stromelysin in the presence of saturating amounts of acetohydroxamic acid. Details of procedures and results of this second identification step are set forth above in Example 2.

The compound identified as a second ligand from these studies and used in subsequent design steps was the compound designated as Compound #4 in Table 1 (See Example 2).

The next step in the design process was to construct a ternary complex of the target stromelysin, the first ligand and the second ligand. This was accomplished by exposing the stromelysin target to the two ligands under conditions that resulted in complex formation. The three-dimensional structure of the ternary complex was then determined using NMR spectroscopy as described below.

The $^{1}$H, $^{13}$C, and $^{15}$N backbone resonances of stromelysin in the ternary complex were assigned from an analysis of several 3D double- and triple-resonance NMR spectra (A. Bax. et al., *Acc. Chem. Res.*, 26: 131–138 (1993)). The $C^\alpha$ resonances of adjacent spin systems were identified from an analysis of three-dimensional (3D) HNCA (L. Kay et al., *J. Magn. Reson.*, 89: 496–514 (1990)) and HN(CO)CA (A. Bax, et al., *J. Bio. NMR*, 1: 99 (1991)) spectra recorded with identical spectral widths of 1773 Hz (35.0 ppm), 3788 Hz (30.1 ppm), and 8333 Hz (16.67 ppm) in the $F_1(^{15}N)$, $F_2(^{13}C)$ and $F_3(^{1}H)$ dimensions, respectively.

The data matrix was $38(t_1) \times 48(t_2) \times 1024(t_3)$ complex points for the HNCA spectrum, and $32(t_1) \times 40(t_2) \times 1024(t_3)$ complex points for the HN(CO)CA spectrum. Both spectra were acquired with 16 scans per increment. A 3D CBCA (CO)NH spectrum (S. Grzesiek, et al., *J. Am. Chem. Soc.*, 114: 6261–6293 (1992)) was collected with $32(t_1, {}^{15}N) \times 48(t_2, {}^{13}C) \times 1024(t_3, {}^{1}H)$ complex points and 32 scans per increment. Spectral widths were 1773 Hz (35.0 ppm), 7575.8 Hz (60.2 ppm), and 8333 Hz (16.67 ppm) in the $^{15}$N, $^{13}$C and $^{1}$H dimensions, respectively.

For all three spectra, the $^{1}$H carrier frequency was set on the water resonance and the $^{15}$N carrier frequency was at 119.1 ppm. The $^{13}$C carrier frequency was set to 55.0 ppm in HNCA and HN(CO)CA experiments, and 46.0 ppm in the CBCA(CO)NH experiment.

The backbone assignments were confirmed from an analysis of the crosspeaks observed in an $^{15}$N-separated 3D NOESY-HSQC spectrum and a 3D HNHA-J spectrum. The $^{15}$N-separated 3D NOESY-HSQC spectrum (S. Fesik, et al., *J. Magn. Reson.*, 87: 588–593 (1988)); D. Marion, et al., *J. Am. Chem. Soc.*, 111: 1515–1517 (1989)) was collected with a mixing time of 80 ms. A total of $68(t_1, {}^{15}N) \times 96(t_2, {}^{1}H) \times 1024(t_3, {}^{1}H)$ complex points with 16 scans per increment were collected, and the spectral widths were 1773 Hz (35.0 ppm) for the $^{15}$N dimension, 6666.6 Hz ($t_2, {}^{1}H$, 13.3 ppm), and 8333 Hz (16.7 ppm) for the $^{1}$H dimension.

The 3D HNHA-J spectrum (G. Vuister, et al., *J. Am. Chem. Soc.*, 115: 7772–7777 (1993)), which was also used to obtain ${}^{3}J_{HNH\alpha}$ coupling constants, was acquired with $35(t_1, {}^{15}N) \times 64(t_2, {}^{1}H) \times 1024(t_3, {}^{1}H)$ complex points and 32 scans per increment. Spectral widths and carrier frequencies were identical to those of the $^{15}$N-separated NOESY-HSQC spectrum. Several of the $H^\beta$ signals were assigned using the HNHB experiment. The sweep widths were the same as in the $^{15}$N-separated NOESY-HSQC spectrum that was acquired with $32(t_1, {}^{15}N) \times 96(t_2, {}^{1}H) \times 1024(t_3, {}^{1}H)$ complex points.

The $^{1}$H and $^{13}$C chemical shifts were assigned for nearly all sidechain resonances. A 3D HCCH-TOCSY spectrum (L. Kay, et al., *J. Magn. Reson.*, 101 b: 333–337 (1993)) was acquired with a mixing time of 13 ms using the DIPSI-2 sequence (S. Rucker, et al., *Mol. Phys.*, 68: 509 (1989)) for $^{13}$C isotropic mixing. A total of $96(t_1, {}^{13}C) \times 96(t_2, {}^{1}H) \times 1024(t_3, {}^{1}H)$ complex data points were collected with 16 scans per increment using a spectral width of 10638 Hz (70.8 ppm, $w_1$), 4000 Hz (6.67 ppm, $w_2$), and 4844 (8.07 ppm, $w_3$). Carrier positions were 40 ppm, 2.5 ppm, and at the water frequency for the $^{13}$C, indirectly detected $^{1}$H, and observed $^{1}$H dimensions, respectively.

Another 3D HCCH-TOCSY study was performed with the $^{13}$C carrier at 122.5 rpm to assign the aromatic residues. The spectra were collected with $36(t_1, {}^{13}C) \times 48(t_2, {}^{1}H) \times 1024(t_3, {}^{1}H)$ complex points with spectral widths of 5263 Hz (35.0 ppm, $w_1$), 3180 Hz (5.30 ppm, $w_2$), and 10,000 (16.7 ppm, $w_3$). Carrier positions were 122.5 ppm, 7.5 ppm, and at the water frequency for the $^{13}$C, indirectly detected $^{1}$H, and observed $^{1}$H dimensions, respectively.

A $^{13}$C-separated 3D NOESY-HMQC spectrum (S. Fesik, et al., *J. Magn. Reson.*, 87: 588–593 (1988)); D. Marion, et al., *J. Am. Chem. Soc.*, 111: 1515–1517 (1989)) was recorded using a mixing time of 75 ms. A total of 80 ($t_1$, $^{13}$C)×72($t_2$, $^1$H)×1024($t_3$, $^1$H) complex data points with 16 scans per increment were collected over spectral widths of 10638 Hz (70.49 ppm, $w_1$), 6666.6 Hz (13.3 ppm, $w_2$), and 8333.3 Hz (16.67 ppm, $w_3$). The $^1$H carrier frequencies were set to the water resonance, and the $^{13}$C carrier frequency was placed at 40.0 ppm.

Stereospecific assignments of methyl groups of the valine and leucine residues were obtained by using a biosynthetic approach (Neri et al., *Biochem.*, 28: 7510–7516 (1989)) on the basis of the $^{13}$C-$^3$C one-bond coupling pattern is observed in a high-resolution $^1$H, $^{13}$C-HSQC spectrum (G. Bodenhausen, et al., *J. Chem. Phys. Lett.*, 69: 185–189 (1980)) of a fractionally $^{13}$C-labeled protein sample. The spectrum was acquired with 200($^{13}$C, $t_1$)×2048($^1$H, $t_2$) complex points over spectral widths of 5000 Hz (39.8 ppm, $^{13}$C) and 8333 Hz (16.7 ppm, $^1$H). Carrier positions were 20.0 ppm for the $^{13}$C dimension, and at the water frequency for the $^1$H dimension.

To detect NOEs between the two ligands and the protein, a 3D $^{12}$C-filtered, $^{13}$C-edited NOESY spectrum was collected. The pulse scheme consisted of a double $^{13}$C-filter sequence (A. Gemmeker, et al., *J. Magn. Reson.*, 96: 199–204 (1992)) concatenated with a NOESY-HMQC sequence (S. Fesik, et al, *J. Magn. Reson.*, 87: 588–593 (1988)); D. Marion, et al., *J. Am. Chem. Soc.*, 111: 1515–1517 (1989)). The spectrum was recorded with a mixing time of 80 ms, and a total of 80 ($t_1$, $^{13}$C)×80 ($t_2$, $^1$H)×1024 ($t_3$, $^1$H) complex points with 16 scans per increment. Spectral widths were 8865 Hz (17.73 ppm, $w_1$), 6667 Hz (13.33 ppm, $w_2$), and 8333 Hz (16.67 ppm, $w_3$), and the carrier positions were 40.0 ppm for the carbon dimension and at the water frequency for both proton dimensions.

To identify amide groups that exchanged slowly with the solvent, a series of $^1$H, $^{15}$N-HSQC spectra (G. Bodenhausen, et al., *J. Chem. Phys. Lett.*, 69: 185–189 (1980)) were recorded at 25° C. at 2 hr intervals after the protein was exchanged into D$_2$O. The acquisition of the first HSQC spectrum was started 2 hrs. after the addition of D$_2$O.

All NMR spectra were recorded at 25° C. on a Bruker AMX500 or AMX600 NMR spectrometer. The NMR data were processed and analyzed on Silicon Graphics computers. In all NMR experiments, pulsed field gradients were applied where appropriate as described (A. Bax, et al., *J. Magn. Reson.*, 99: 638 (1992)) to afford the suppression of the solvent signal and spectral artifacts. Quadrature detection in indirectly detected dimensions was accomplished by using the States-TPPI method (D. Marion, et al., *J. Am. Chem. Soc.*, 111: 1515–1517 (1989)). Linear prediction was employed as described (E. Olejniczak, et al., *J. Magn. Reson.*, 87: 628–632 (1990)).

The derived three-dimensional structure of the ternary complex was then used to define the spatial orientation of the first and second ligands to each other as well as to the target stromelysin molecule.

Distance restraints derived from the NOE data were classified into six categories based on the NOE cross peak intensity and given a lower bound of 1.8 Å and upper bounds of 2.5 Å, 3.0 Å, 3.5 Å, 4.0 Å, 4.5 Å, and 5.0 Å, respectively. Restraints for φ torsional angles were derived from $^3J_{HNH\alpha}$ coupling constants measured from the 3D HNHA-J spectrum (G. Vuister, et al., *J. Am. Chem. Soc.*, 115: 7772–7777 (1993)). The φ angle was restrained to 120%±40% for $^3J_{HNH\alpha}$22 8.5 Hz, and 60%±40% for $^3J_{HNH\alpha}$<5 Hz.

Hydrogen bonds, identified for slowly exchanging amides based on initial structures, were defined by two restraints: 1.8–2.5 Å for the H-O distance and 1.8–3.3 Å for the N-O distance. Structures were calculated with the X-PLOR 3.1 program (A. Bruinger, "XPLOR 3.1 Manual," Yale University Press, New Haven, 1992) on Silicon Graphics computers using a hybrid distance geometry-simulated annealing approach (M. Nilges, et al., *FEBS lett.*, 229: 317–324 (1988)).

A total of 1032 approximate interproton distance restraints were derived from the NOE data. In addition, 21 unambiguous intermolecular distance restraints were derived from a 3D 12C-filtered, 13C-edited NOESY spectrum. Of the 1032 NOE restraints involving the protein, 341 were intra-residue, 410 were sequential or short-range between residues separated in the primary sequence by less than five amino acids, and 281 were long-range involving residues separated by at least five residues.

In addition to the NOE distance restraints, 14 φ dihedral angle restraints were included in the structure calculations that were derived from three-bond coupling constants ($^3J_{HNH\alpha}$) determined from an HNHA-J spectrum (G. Viioster, et al., *J. Am. Chem. Soc.*, 115: 7772–7777 (1993)). The experimental restraints also included 120 distance restraints corresponding to 60 hydrogen bonds. The amides involved in hydrogen bonds were identified based on their characteristically slow exchange rate, and the hydrogen bond partners from initial NMR structures calculated without the hydrogen bond restraints. The total number of non-redundant, experimentally-derived restraints was 1166.

The structures were in excellent agreement with the NMR experimental restraints. There were no distance violations greater than 0.4 Å, and no dihedral angle violations greater than 5 degrees. In addition, the simulated energy for the van der Waals repulsion term was small, indicating that the structures were devoid of bad inter-atomic contacts.

The NMR structures also exhibited good covalent bond geometry, as indicated by small bond-length and bond-angle deviations from the corresponding idealized parameters. The average atomic root mean square deviation of the 8 structures for residues 93–247 from the mean coordinates was 0.93 Å for backbone atoms ($C^\alpha$, N, and C'), and 1.43 Å for all non-hydrogen atoms.

Figure 10:
FIG. 10 shows a ribbon plot of a ternary complex of first and second ligands bound to the catalytic domain of stromelysin.

A ribbon plot of the ternary complex involving stromelysin, acetohydroxamic acid (the first ligand), and the second ligand is shown in FIG. 10. The structure is very similar to the global fold of other matrix metalloproteinases and consists of a five-stranded β-sheet and three a-helices.

The catalytic zinc was located in the binding pocket. It was coordinated to three histidines and the two oxygen atom of acetohydroxamic acid. A biaryl group of the second ligand was located in the S1' pocket between the second helix and the loop formed from residues 218–223. This deep and narrow pocket is lined with hydrophobic residues which make favorable contacts with the ligand.

Based on the three-dimensional structure of the ternary complex as determined above and the structure/activity relationships observed for the binding to stromelysin of structural analogs of the second ligand (i.e., other biaryl compounds), new molecules were designed that linked together the acetohydroxamic acid to biaryls.

As shown in Table 4 below, the initial biaryls chosen contained an oxygen linker and the absence or presence of CN para to the biaryl linkage. Initial linkers contained varying lengths of methylene units. Means for linking compounds with linkers having varying lengths of methylene units are well known in the art.

TABLE 4

[Structure: HO-N(H)-C(=O)-X-O-C6H4-C6H4-R]

| Compound Inhibition | X | R | Stromelysin |
|---|---|---|---|
| 21 | $(CH_2)_2$ | H | 0.31 µM |
| 22 | $(CH_2)_3$ | H | 110 µM |
| 23 | $(CH_2)_4$ | H | 38% @ 100 µM |
| 24 | $(CH_2)_5$ | H | 43% @ 100 µM |
| 25 | $(CH_2)_2$ | CN | 0.025 µM |
| 26 | $(CH_2)_3$ | CN | 3.4 µM |

TABLE 4-continued

[Structure: HO-N(H)-C(=O)-X-O-C6H4-C6H4-R]

| Compound Inhibition | X | R | Stromelysin |
|---|---|---|---|
| 27 | $(CH_2)_4$ | CN | 3.5 µM |
| 28 | $(CH_2)_5$ | CN | 1.7 µM |

As expected based on the better binding of the CN substituted biaryls to stromelysin, the CN derivatives exhibited better stromelysin inhibition. The compound that exhibited the best inhibition of stromelysin contained a linker with two methylene units.

The present invention has been described with reference to preferred embodiments. Those embodiments are not limiting of the claims and specification in any way. One of ordinary skill in the art can readily envision changes, modifications and alterations to those embodiments that do not depart from the scope and spirit of the present invention.

What is claimed is:

1. A process of designing a drug that serves as a ligand to a given target molecule comprising the steps of:
   a) identifying a first ligand to the target molecule using two-dimensional $^{15}$N/$^1$H NMR correlation spectroscopy;
   b) identifying a second ligand to the target molecule using two-dimensional $^{15}$N/$^1$H NMR correlation spectroscopy;
   c) forming a ternary complex by binding the first and second ligands to the target molecule;
   d) determining the three dimensional structure of the ternary complex and thus the spatial orientation of the first and second ligands on the target molecule; and
   e) linking the first and second ligands to form the drug, wherein the spatial orientation of step (d) is maintained.

2. The process of claim 1 wherein the identification of the first ligand is accomplished by generating a first two-dimensional $^{15}$N/$^1$H NMR correlation spectrum of a uniformly $^{15}$N-labeled target molecule, exposing the labeled target molecule to one or more chemical compounds, generating a separate two-dimensional $^{15}$N/$^1$H NMR correlation spectrum for each of the compounds, and comparing each spectrum to the first spectrum to determine whether differences in those spectra exist, which differences would indicate the presence of a first ligand that has bound to the target molecule.

3. The process of claim 1 wherein the identification of the second ligand is accomplished by generating a first two-dimensional $^{15}$N/$^1$H NMR correlation spectrum of a uniformly $^{15}$N-labeled target molecule, exposing the labeled target molecule to one or more chemical compounds, generating a separate two-dimensional $^{15}$N/$^1$H NMR correlation spectrum for each of the compounds, and comparing each spectrum to the first spectrum to determine whether differences in those spectra exist, which differences would indicate the presence of a second ligand that has bound to the target molecule.

4. The process of claim 3 wherein the target molecule is bound to the first ligand before being exposed to the compounds.

5. The process of claim 2 wherein the differences in the two-dimensional $^{15}$N/$^1$H NMR correlation spectra are chemical shifts at particular $^{15}$N-labeled sites in the target molecule and chemical shifts in protons attached to those $^{15}$N-labeled sites.

6. The process of claim 3 wherein the differences in the two-dimensional $^{15}$N/$^1$H NMR correlation spectra are chemical shifts at particular $^{15}$N-labeled sites in the target molecule and chemical shifts in protons attached to those $^{15}$N-labeled sites.

7. The process of claim 1 wherein the three dimensional structure of the ternary complex is determined using NMR spectroscopy or X-ray crystallography.

8. The process of claim 1 wherein the target molecule is a polypeptide.

* * * * *

UNITED STATES PATENT AND TRADEMARK OFFICE
CERTIFICATE OF CORRECTION

PATENT NO. : 5,891,643
DATED : April 6, 1999
INVENTOR(S) : Stephen W. Fesik, et. al.

It is certified that error appears in the above-identified patent and that said Letters Patent is hereby corrected as shown below:

Col. 1, line 7
replace "the the "
with --the--.

Col. 12, line 61
replace "ATAGGATCCG-"
with --ATAGGATCCT---.

Col. 12, line 62
replace "FAGGT..."
with --TAGGT...--.

Col. 23, line 67
replace "22"
with -->--.

Signed and Sealed this

Twenty-fifth Day of July, 2000

*Attest:*

Q. TODD DICKINSON

*Attesting Officer*     *Director of Patents and Trademarks*